United States Patent
Vo-Dinh et al.

(10) Patent No.: US 12,429,426 B2
(45) Date of Patent: Sep. 30, 2025

(54) SPATIALLY OFFSET HYPERSPECTRAL IMAGING SYSTEMS AND METHODS THEREOF

(71) Applicant: Duke University, Durham, NC (US)

(72) Inventors: Tuan Vo-Dinh, Durham, NC (US); Ren Odion, Durham, NC (US)

(73) Assignee: DUKE UNIVERSITY, Durham, NC (US)

( * ) Notice: Subject to any disclaimer, the term of this patent is extended or adjusted under 35 U.S.C. 154(b) by 90 days.

(21) Appl. No.: 18/212,955

(22) Filed: Jun. 22, 2023

(65) Prior Publication Data

US 2023/0417677 A1   Dec. 28, 2023

Related U.S. Application Data

(60) Provisional application No. 63/355,720, filed on Jun. 27, 2022.

(51) Int. Cl.
  G01N 21/65 (2006.01)
  A61B 5/00 (2006.01)
  (Continued)

(52) U.S. Cl.
  CPC ....... G01N 21/658 (2013.01); G01N 33/0098 (2013.01); G01N 33/4833 (2013.01);
  (Continued)

(58) Field of Classification Search
  CPC .. G01N 21/658; G01N 21/65; G01N 21/4795; G01N 2021/4709;
  (Continued)

(56) References Cited

U.S. PATENT DOCUMENTS 9,927,364 B1 * 3/2018 Chao ............... G01N 21/65
2008/0129992 A1 * 6/2008 Matousek ......... G01N 21/65
                                                   356/301

(Continued)

OTHER PUBLICATIONS

Jing Luo, Shuo Li, Erik Forsberg, and Sailing He, "4D surface shape measurement system with high spectral resolution and great depth accuracy," Opt. Express 29, 13048-13070 (2021) (Year: 2021).*

Primary Examiner — Tarifur R Chowdhury
Assistant Examiner — Kaitlyn E Kidwell
(74) Attorney, Agent, or Firm — NK Patent Law

(57) ABSTRACT

A method for spatially locating a target inside a sample and providing spectral information for imaging the target includes illuminating a light source onto a sample to produce a backscattered optical signal; spectrally scanning and detecting the backscattered optical signal at selected spectral increments using a rapid wavelength-tuning solid-state device; providing three-dimensional spectral information (x, y, wavelength) from the sample at a series of wavelengths of interest; spatially scanning the backscattered signal in a two-dimensional plane at selected spatial increments; providing three-dimensional spatial information (x, y, z) from the sample at a series of spatial dimensions of interest; and combining the three-dimensional spatial information and the three-dimensional spatial information to produce a four-dimensional (x, y, z, and wavelength) data hypercube for use in collecting data from inside the sample.

19 Claims, 20 Drawing Sheets

(51) Int. Cl.
- *A61B 5/1495* (2006.01)
- *G01N 21/47* (2006.01)
- *G01N 21/64* (2006.01)
- *G01N 33/00* (2006.01)
- *G01N 33/483* (2006.01)

(52) U.S. Cl.
CPC .......... *A61B 5/0075* (2013.01); *A61B 5/0077* (2013.01); *A61B 5/1495* (2013.01); *G01N 2021/4709* (2013.01); *G01N 2021/4742* (2013.01); *G01N 21/4795* (2013.01); *G01N 21/6489* (2013.01); *G01N 21/65* (2013.01); *G01N 2201/06113* (2013.01)

(58) Field of Classification Search
CPC .......... G01N 33/0098; G01N 33/4833; G01N 2201/06113; G01N 2021/4742; G01N 21/6489; A61B 5/0075; A61B 5/0077; A61B 5/1495
See application file for complete search history.

(56) References Cited

U.S. PATENT DOCUMENTS

| | | | |
|---|---|---|---|
| 2009/0245605 A1* | 10/2009 | Levenson | G01N 21/255 382/128 |
| 2010/0016783 A1* | 1/2010 | Bourke, Jr. | A61P 1/04 378/65 |
| 2011/0021970 A1* | 1/2011 | Vo-Dinh | A61B 5/4848 424/490 |
| 2013/0114070 A1* | 5/2013 | Gardner, Jr. | G01J 3/0221 356/73 |
| 2017/0059408 A1* | 3/2017 | Körner | G01J 3/0229 |
| 2018/0042483 A1* | 2/2018 | Bardhan | G01J 3/2823 |
| 2018/0202935 A1* | 7/2018 | Bahlman | G02B 21/0076 |
| 2020/0284657 A1* | 9/2020 | Leblond | G01J 3/0218 |

\* cited by examiner

SPATIALLY OFFSET HYPERSPECTRAL IMAGING SYSTEMS AND METHODS THEREOF

CROSS-REFERENCE TO RELATED APPLICATIONS

This application claims priority to U.S. Provisional Patent Application No. 63/355,720, filed on Jun. 27, 2022, which is incorporated by reference herein in its entirety.

STATEMENT REGARDING FEDERALLY SPONSORED RESEARCH OR DEVELOPMENT

This invention was made with government support under Federal Grant No. DE-SC0019393 awarded by the U.S. Department of Energy. The government has certain rights in the invention.

BACKGROUND

There are a wide variety of spectroscopic techniques ranging from infrared/UV absorption and adaptive optics multiphoton microscopy to fluorescence, and Raman techniques (conventional, nonlinear, plasmonics-enhanced) have played an important role in the analysis of a wide variety of samples due to their non-invasive nature. Conventional optical methods, however, are usually limited in obtaining signals at the surface level, due to the attenuation caused by the highly scattering and absorbing sample media.

Challenges to deep sample imaging have necessitated the development of special techniques such as spatially offset optical spectroscopy to collect signals that have travelled through several layers of tissue. However, these techniques provide only spectral information in one dimension (i.e., depth). There is a strong need to develop practical, efficient, sensing and imaging methods to detect analytes of interest deep inside samples such as tissue, substrates, and/or materials being monitored.

SUMMARY

In a first aspect of the invention, a method for spatially locating a target inside a sample and providing spectral information for imaging the target comprises illuminating a light source onto a sample to produce a backscattered optical signal; spectrally scanning and detecting the backscattered optical signal at selected spectral increments using a rapid wavelength-tuning solid-state device; providing three-dimensional spectral information (x, y, wavelength) from the sample at a series of wavelengths of interest; spatially scanning the backscattered signal in a two-dimensional plane at selected spatial increments; providing three-dimensional spatial information (x, y, z) from the sample at a series of spatial dimensions of interest; and combining the three-dimensional spectral information and the three-dimensional spatial information to produce a four-dimensional (x, y, z, and wavelength) data hypercube for use in collecting data from inside samples.

In a feature of this aspect, the light source is a laser. In another feature of this aspect, the the rapid wavelength-tuning solid-state device comprises a liquid crystal tunable filter. The rapid wavelength-tuning solid-state device may comprise an acousto-optic tunable filter. Regarding the first aspect, the light source remotely illuminates the sample, and the detection is performed remotely.

In an additional feature of this aspect, the backscattered signal results from optical techniques exhibiting narrowband spectral structures. The optical techniques may comprise Raman spectroscopy, luminescence spectroscopy, two-photon luminescence, emission spectroscopy, X-ray emission spectroscopy, and time-resolved spectroscopy. The optical techniques may comprise Raman spectroscopy and luminescence from quantum dots, rare earth species, and upconverting nanomaterials.

In another feature of this aspect, the backscattered signal is enhanced with Surface-Enhanced Raman Spectroscopy (SERS) nanoparticles. The SERS nanoparticles may comprise gold nanostars. In an additional feature, the target is a chemical inside a sample container. In another feature, the target is a lesion or tumor inside ex vivo or in vivo tissue of a human or animal. In yet another feature, the target is a biomarker or a sensor inside a living plant. For example, the sensor is a plasmonics-active inverse molecular sentinel nanoprobe based on SERS.

In a second aspect of the invention, a method for producing a multidimensional data hypercube to spatially locate a target inside a sample comprises illuminating a light source from an excitation source onto a sample to produce a backscattered optical signal; spatially scanning and detecting the optical signal to provide spatial data in the x and y dimension; wherein the x and y dimension spatial data are binned according to digital offsets based on selected radial pixel distances from the excitation source; spectrally scanning the optical signal and using spatial offset techniques to provide spatial data in the z direction; and spectrally scanning the optical signal and using a rapid wavelength-tuning solid-state filter to provide data in the spectral dimension, wherein the x and y dimension spatial data, the z dimension spatial data, and the data in the spectral dimension are used to produce a multidimensional hyperspectral data hypercube.

In a feature of this aspect, the light source is a laser. In another feature of this aspect, the rapid wavelength-tuning solid-state device comprises a liquid crystal tunable filter. In yet another feature of this aspect, the rapid wavelength-tuning solid-state device comprises an acousto-optic tunable filter.

In an additional feature, the light source is remotely illuminating the sample and the detection is performed remotely. In yet another feature, the target is a chemical inside a container. In a further feature, the target is a lesion or tumor inside ex vivo or in vivo tissue of a human or animal or is a biomarker or sensor inside a living plant.

BRIEF DESCRIPTION OF THE DRAWINGS

The accompanying Figures and Examples are provided by way of illustration and not by way of limitation. The foregoing aspects and other features of the disclosure are explained in the following description, taken in connection with the accompanying example figures (also "FIG.") relating to one or more embodiments.

DETAILED DESCRIPTION

Figure 1:
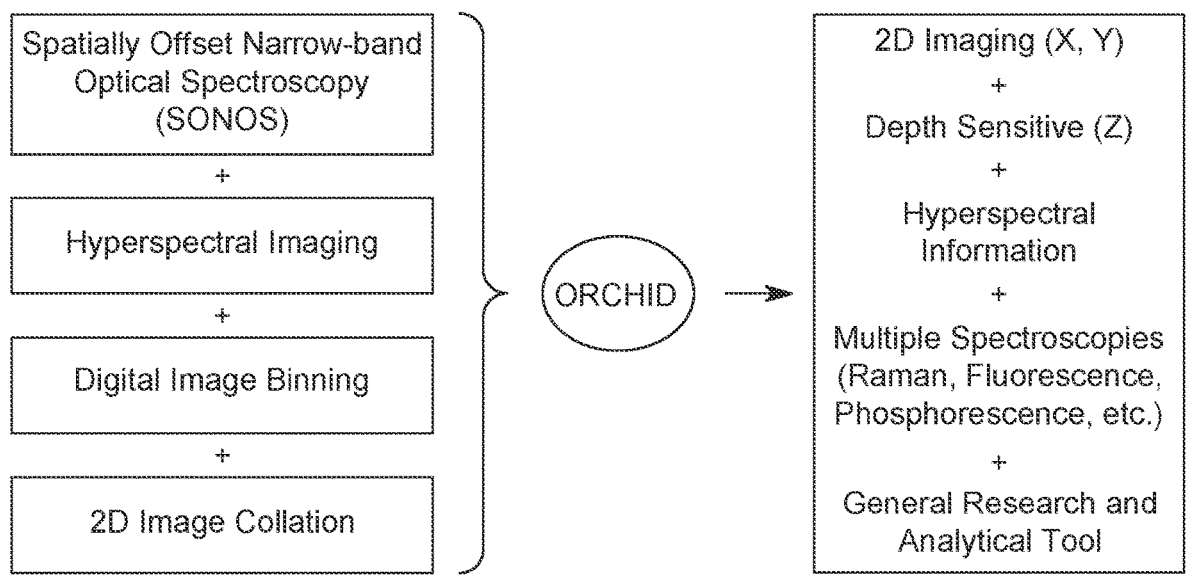
FIG. 1 is a schematic diagram of an embodiment of the ORCHID method and system.

To promote an understanding of the principles of the present disclosure, reference will now be made to preferred embodiments and specific language will be used to describe the same. It will nevertheless be understood that no limitation of the scope of the disclosure is thereby intended, such alteration and further modifications of the disclosure as illustrated herein, being contemplated as would normally occur to one skilled in the art to which the disclosure relates.

Articles "a" and "an" are used herein to refer to one or to more than one (i.e., at least one) of the grammatical object of the article. By way of example, "an element" means at least one element and can include more than one element.

"About" is used to provide flexibility to a numerical range endpoint by providing that a given value may be "slightly above" or "slightly below" the endpoint without affecting the desired result.

The use herein of the terms "including," "comprising," or "having," and variations thereof, is meant to encompass the elements listed thereafter and equivalents thereof as well as additional elements. As used herein, "and/or" refers to and encompasses any and all possible combinations of one or more of the associated listed items, as well as the lack of combinations when interpreted in the alternative ("or").

As used herein, the transitional phrase "consisting essentially of" (and grammatical variants) is to be interpreted as encompassing the recited materials or steps "and those that do not materially affect the basic and novel characteristic(s)" of the claimed invention. Thus, the term "consisting essentially of" as used herein should not be interpreted as equivalent to "comprising."

Moreover, the present disclosure also contemplates that in some embodiments, any feature or combination of features set forth herein can be excluded or omitted. To illustrate, if the specification states that a complex comprises components A, B and C, it is specifically intended that any of A, B or C, or a combination thereof, can be omitted and disclaimed singularly or in any combination.

Recitation of ranges of values herein are merely intended to serve as a shorthand method of referring individually to each separate value falling within the range, unless otherwise indicated herein, and each separate value is incorporated into the specification as if it were individually recited herein. For example, if a concentration range is stated as 1% to 50%, it is intended that values such as 2% to 40%, 10% to 30%, or 1% to 3%, etc., are expressly enumerated in this specification. These are only examples of what is specifically intended, and all possible combinations of numerical values between and including the lowest value and the highest value enumerated are to be considered expressly stated in this disclosure.

Unless otherwise defined, all technical terms used herein have the same meaning as commonly understood by one of ordinary skill in the art to which this disclosure belongs.

Described herein is a general and practical sensing method, referred to as Optical Recognition of Constructs Using Hyperspectral Imaging and Detection (ORCHID). The sensing method integrates (1) the spatial offset detection concept by computationally binning 2D optical data associated with digital offsets based on selected radial pixel distances from the excitation source; (2) hyperspectral imaging using a tunable filter; and (3) digital image binning and collation. ORCHID is a versatile method that collects optical signals deep inside samples across three spatial (X, Y, Z) as well as spectral dimensions. The ORCHID method is applicable to various optical techniques that exhibit narrowband structures. Exemplary optical techniques include, without limitation, Raman spectroscopy, luminescence spectroscopy, two-photon luminescence, emission spectroscopy, X-ray emission spectroscopy, and time-resolved spectroscopy. Luminescence spectroscopy methods can include quantum dot luminescence. In the ORCHID method, a light source is illuminated onto a sample to produce a backscattered optical signal that is detected. For Raman scattering, a laser light source is used. For luminescence spectroscopy, e.g., quantum dot luminescence, other light sources can be used. In embodiments, the light source is remotely illuminating the sample and detection of the backscattered optical signal is performed remotely. In the Examples below, samples containing surface enhanced Raman scattering (SERS)-active gold nanostar probes and quantum dots embedded in gel were used to show how the ORCHID system and method can be used. The ORCHID system and method produces a hyperspectral data hypercube that can be used to spatially locate a target emitting nanoparticle volumes and provide spectral information for in-depth 3D imaging.

In embodiments, ORCHID is a method for spatially locating a target inside a sample and providing spectral information for imaging the target. The target can be a chemical inside a sample container. The target can also be a lesion or a tumor inside in vivo or ex vivo tissue of a human or animal or a sensor inside a living plant. The method comprises illuminating a light source onto a sample to produce a backscattered optical signal; spectrally scanning and detecting the backscattered optical signal at selected spectral increments using a rapid wavelength-tuning solid-state device; providing three-dimensional spectral information (x, y, wavelength) from a sample at a series of wavelengths of interest; spatially scanning the backscattered signal in a two-dimensional plane at selected spatial increments; providing three-dimensional spatial information (x, y, z) from a sample at a series of spatial dimensions of interest; and combining the three-dimensional spectral information and the three-dimensional spatial information to produce a four-dimensional (x, y, z, and wavelength) data hypercube for use in collecting data from inside samples.

FIG. 1 is a schematic diagram of an embodiment of the ORCHID method and system. The ORCHID system and method is an integration of different techniques: (I) spatial offset detection concept, (II) hyperspectral imaging, (III) digital image binning, and (IV) 3D image collation. Spatially offset methods include techniques that are used to selectively collect signal from deeper layers in a sample. Hyperspectral imaging integrates the spatial information collected from the spatially offset methods with spectral information to produce an information rich multidimensional dataset. Digital Image Binning and 2D Image Collation complete the ORCHID methodology by integrating post processing techniques and producing a hyperspectral data hypercube that can be used to assemble signals with positions on the sample.

ORCHID expands the spatial offset methodology into a 3D imaging method in the XY plane and Z depth. In embodiments, this can be done by combining a hyperspectral imaging system using a rapid wavelength-tuning solid-state filter, such as a spectrally scanned liquid crystal tunable filter (LCTF), and a two-dimensional charge coupled device (CCD). With ORCHID, the recorded intensity data collected on the CCD are digitally binned within circular rings at different pixel radial distances from the excitation spot as a digital strategy for obtaining the different source to detector spatial offsets. The result is a map of multiple hyperspectral data hypercubes that contain information on the spatial and spectral location of the SERS signal of the target. The Examples demonstrate the ORCHID system's capabilities by showing its ability to discern SERS signatures of different embedded GNS-dyes in agarose gel layers. The Examples show a mapping capability over a large field of view region of a gel to show the potential for hyperspectral imaging. The procedure represents a novel method for depth sensitive molecular imaging of tumor margins and provides a new development towards more accessible early cancer detection.

The ORCHID method can provide a versatile, efficient method to detect, monitor, and image target species deep inside samples. Although the detection method discussed herein involve Raman and surface-enhanced Raman scattering (SERS) techniques, a person having ordinary skill in the art will understand that the concept can be applied to other spectroscopic techniques that exhibit narrow-band structures, such as Raman scattering as well as luminescence from quantum dots, rare earth species, and upconverting nanomaterials.

SERS techniques and plasmonic nanoprobes have been used for a wide variety of chemical analysis, biological monitoring, and medical applications. Nanoparticles made of noble metal (silver, gold) exhibit enormous Raman signal enhancement due to the so-called "plasmonic" effect producing a strong electromagnetic (EM) field enhancement near the nanoparticle's surface, producing the SERS effect, which has been shown to achieve single-molecule detection.

By coupling a Raman active dye with a metallic nanoparticle with a unique geometry such as a gold nanostar (GNS), a very strong SERS enhancement can occur due to the "lightning rod" effect on the sharp tips of the nanoparticles. This nanoparticle platform has been developed as a means of nucleic acid biomarker detection of several diseases and photothermal heat treatment of cancer. The SERS technique has been used for the detection of Raman-labeled GNS absorbed in tumors for in vivo cancer monitoring using a murine model. However, these applications illustrate the selective detection of SERS signals only in one dimension.

To overcome this limitation, the technique Spatially Offset Raman Spectroscopy (SORS) can be used to selectively collect Raman scattered photons that have originated from deeper in the sample by creating a separation between the source and the detector. SORS is a method capable of obtaining subsurface signals by offsetting the laser excitation spot from the collection point and retrieval of photons from deep layers by allowing the photons to have more scattering events before returning to the surface to be collected. With increasing spatial offset, the photon contribution of the top layer decreases much faster than that of the bottom layer. In embodiments, multivariate statistics, such as principal component analysis, can then be used on the offset SORS signal to separate the different signal layers if the Raman signal is known a-priori. SORS has been used in a wide variety of applications ranging from detecting drugs, analyzing bone composition, and inspecting dyes in paintings.

Additionally, SERS-GNS nanoplatforms can be coupled with the Spatially Offset Raman Spectroscopy (SORS) technique as a means of detecting specific spectrochemical signatures of SERS-labeled nanoprobes, such as gold nanostars, through highly scattering tissue material such as bone tissue (e.g., below 5-mm bone of a macaque skull). The methodology described herein can be applied not only to Raman but also to other optical techniques exhibiting narrow-band spectral structures such as luminescence from quantum dots, rare earth species and upconverting nanomaterials. The method is referred to as Spatially Offset of Narrowband Optical Spectroscopy (SONOS), which comprises SORS as well as other types of spatially offset luminescence spectroscopy (SOLS) from quantum dots, rare earth species and upconverting nanomaterials. SONOS advantageously produces sharp spectral peaks that do not overlap, thus allowing for higher multiplexing capabilities and higher signal to noise ratio.

SERS particles can be used as a means of detecting through the skull up to 50 mm deep and show the potential for detecting deeply seated brain cancer tumors once nanoparticles have selectively collected around the tissue.

Figure 2A:
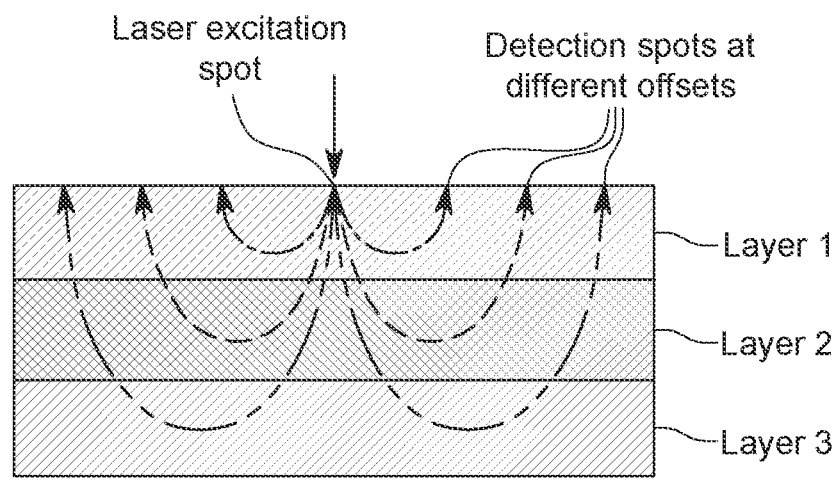
FIG. 2A is a schematic illustration of a lateral view of the collection of offset Raman signals.
Figure 2B:
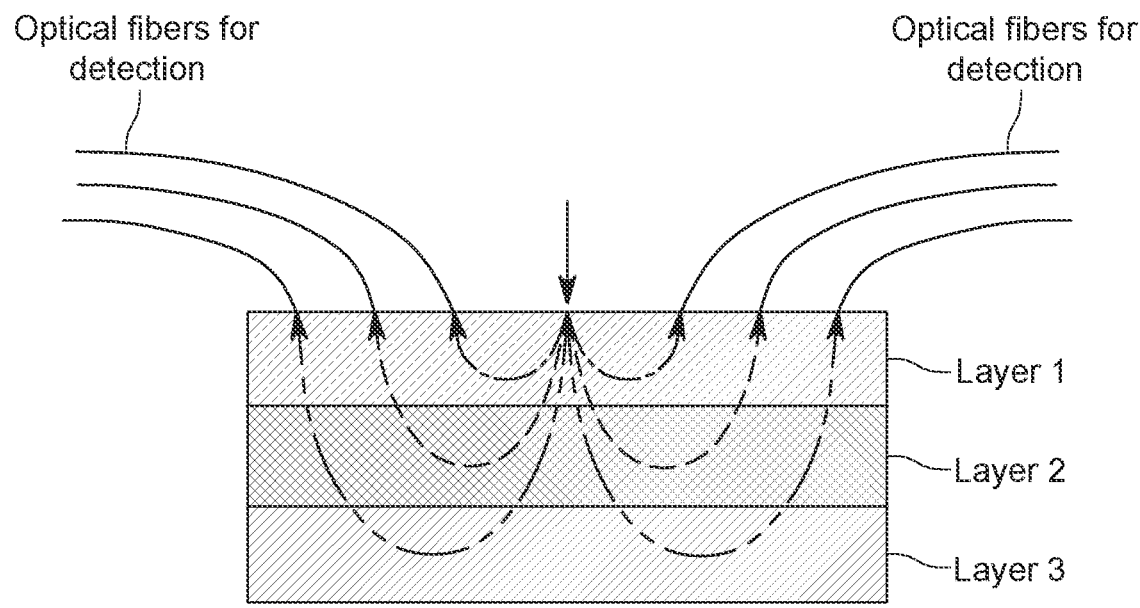
FIG. 2B is a schematic illustration of a lateral view of the collection of offset Raman signals.

The spatially offset method of SONOS, which can be applied to Raman and luminescence, is reliant on the calibration of spectra of different source-to-detector separations. This spectral calibration process is most reliable with spectra exhibiting narrowband emission. Spatial offsets in most SONOS systems physically separate the focal excitation spot from the collection spot in specific distances. The spatially offset strategy can be achieved using two lenses whose focal spots are physically separated, while other configurations using a ringed excitation of specific radial amounts can serve as the offset. An optical fiber bundle may also be used in a similar manner wherein the excitation and collection fibers can be physically separated from each other. FIGS. 2A and 2B are schematic illustrations of a lateral view of the collection of offset Raman signals. While a fiber bundle with different radial collection fibers can be used to effectively collect the different spatial offsets at once, this technique requires the use of a custom-made fiber bundle and is effectively sampling only one spot at a time, providing information in one z-dimension (depth).

Figure 3A:
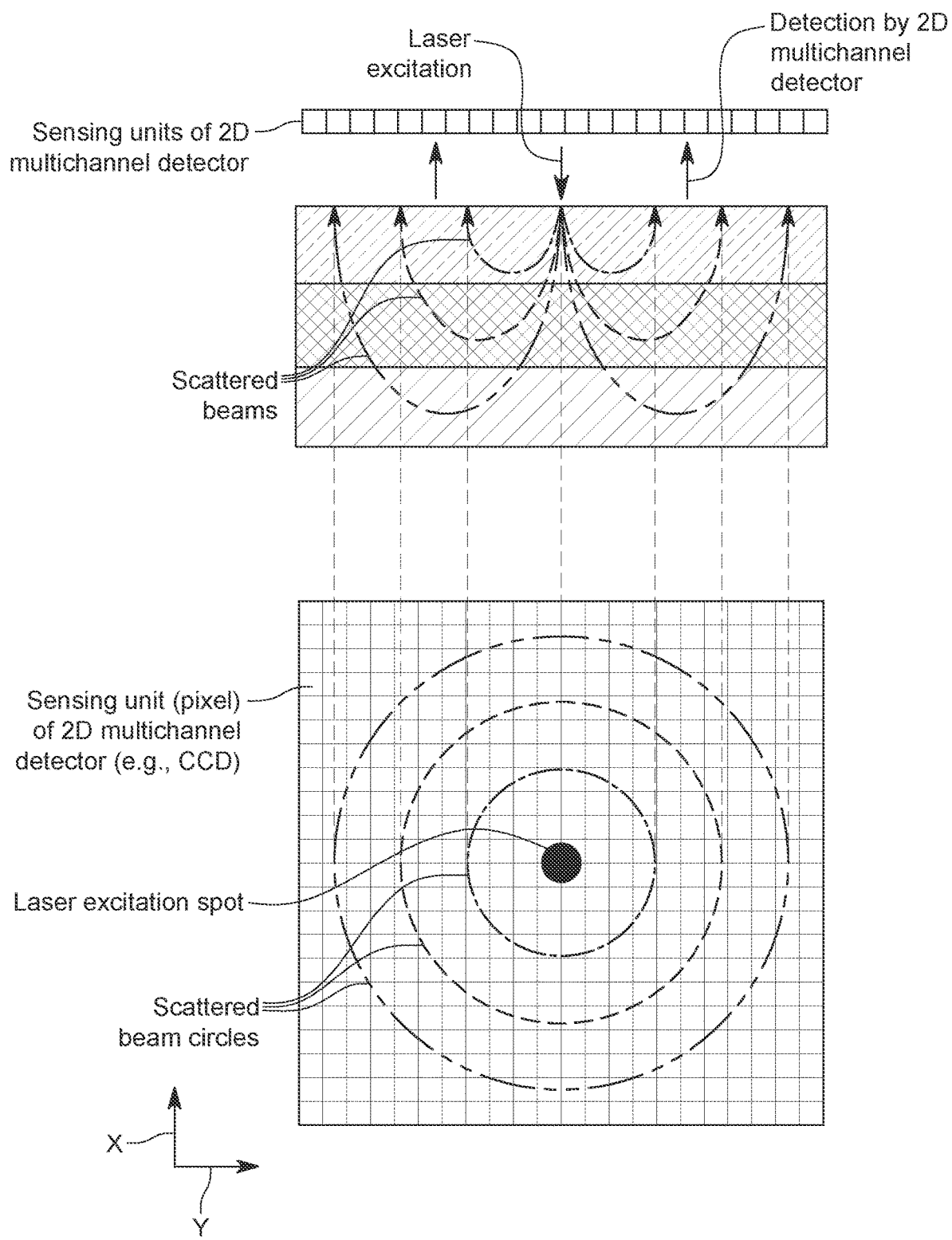
FIG. 3A Instead, the ORCHID system relies on computationally separated pixels that are at specific radial distances from the center of the two-dimensional CCD detector (FIG. 3A).
Figure 3B:
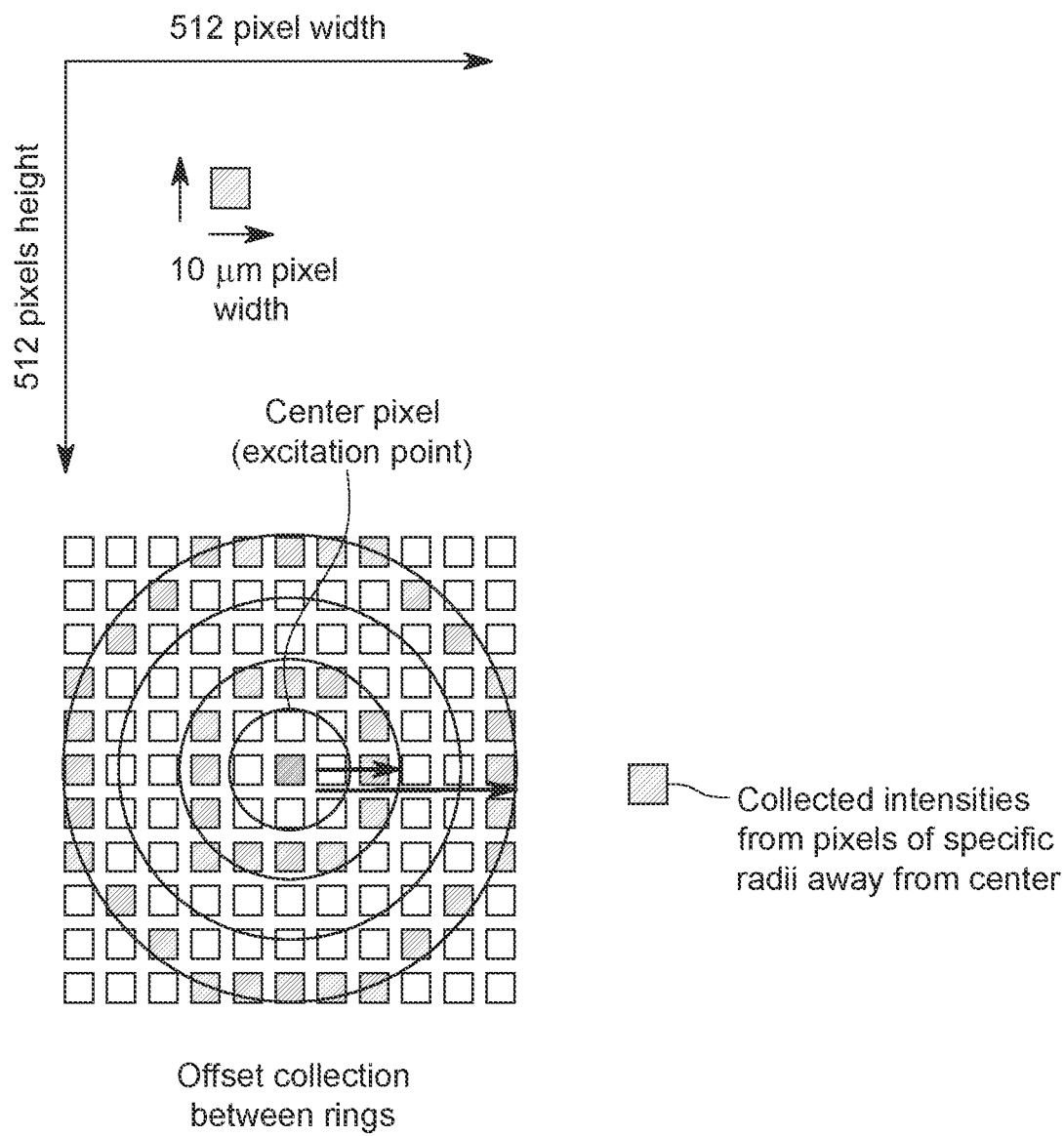
FIG. 3B is a mapping of spatial offsets from a lateral slice to the imaging detector.
Figure 3C:
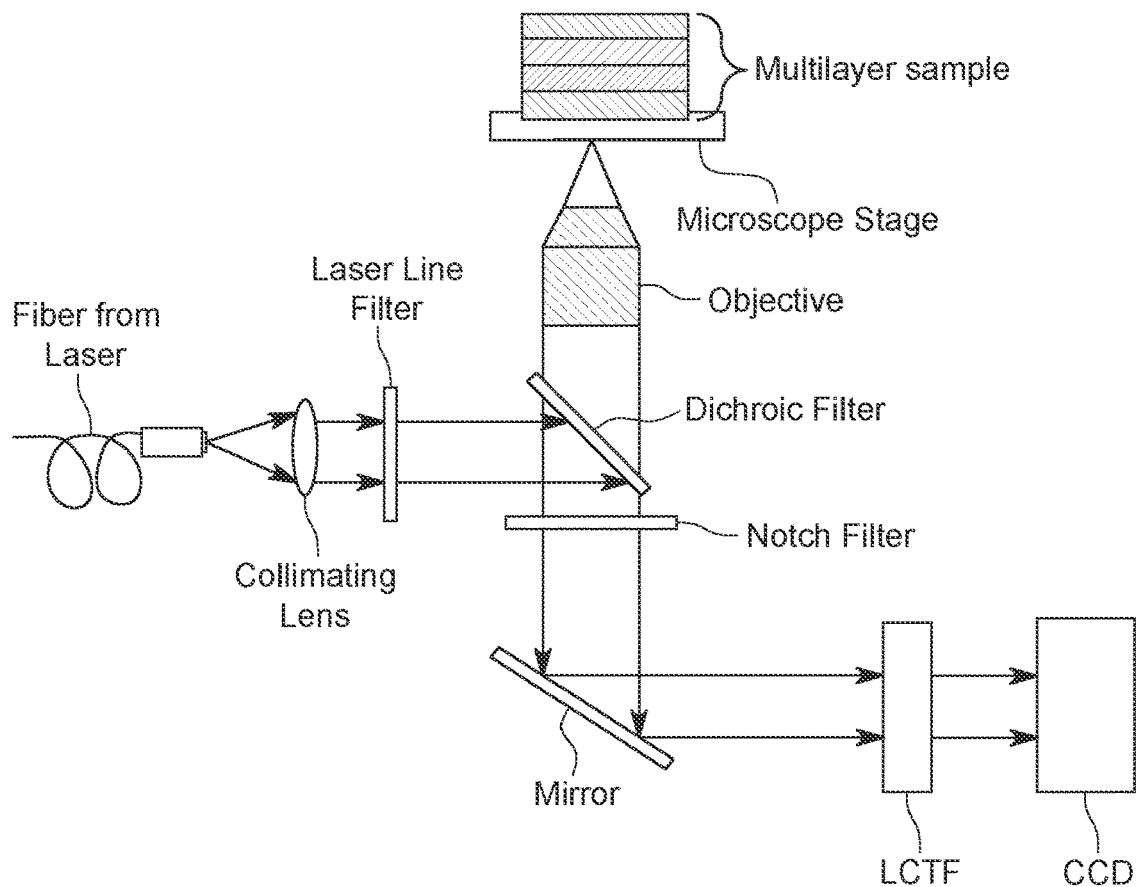
FIG. 3C is a schematic representation of the ORCHID instrumental setup with a multilayer sample.

Advantageously, the ORCHID system does not require a fiber bundle with different radial collection fibers to achieve the offset separating mechanism. Instead, the ORCHID system relies on computationally separated pixels that are at specific radial distances from the center of the two-dimensional CCD detector (FIG. 3A). The CCD with a pixel width of 10 μm and a total of 512×512 pixels can be radially binned at specific distances from the center by computationally selecting pixels at set distances, representing the spatial offsets of SONOS (FIG. 3B). FIG. 3B is a mapping of spatial offsets from a lateral slice to the imaging detector. FIG. 3C is a schematic representation of the ORCHID instrumental setup with a multilayer sample.

Figure 3D:
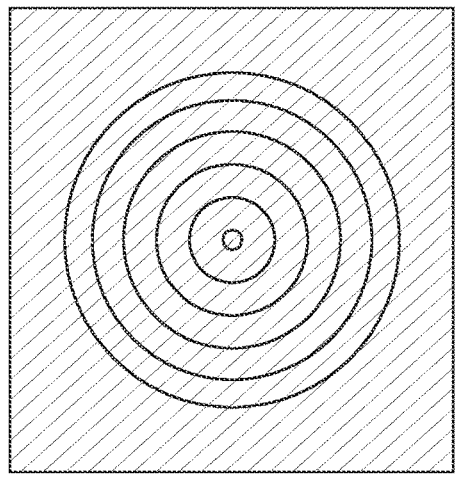
FIG. 3D is an illustration of the binary radial mask used to bin the CCD image data to isolate the pixels of specific spatial offset using different radial rings.

The ORCHID optical system shown in FIG. 3C comprises an inverted optical microscope setup (Olympus Corporation, Shinjuku, Tokyo, Japan) coupled with a 785-nm laser that is collimated and sent to a dichroic mirror configuration where it is focused with a 10-× objective (Thorlabs, New Jersey, USA) towards a sample seated on a motorized linear stage (Zaber Technologies Inc., Vancouver, British Columbia, Canada). The backscattered signal is collected and passed through a Notch filter before going through a spectrally scanned dual-LCTF system mounted in front of a two-dimensional (512×512 pixels) CCD array (Princeton Instruments, New Jersey, USA). The Liquid Crystal Tunable Filters (LCTFs) are programmatically scanned at selected spectral increments (e.g., 1 nm) and at a selected exposure time (e.g., 1 s). The sample is then spatially scanned in the XY plane using the motorized stage at selected increments (5 mm or less) to produce a spatial map that can localize the placement of small gel targets of 5 mm width within a larger gel volume. The resolution in the XY plane may reach optical resolutions of about 1 μm with smaller spatial increments, while Z axis resolution can be several microns depending on the sample size and the desired spatial resolution. FIG. 3D shows the digital binary radial mask used to bin the CCD image data to isolate the pixels of specific spatial offset using different radial rings. These spatially offset pixels are later used to produce spatially offset maps and spectra.

Figure 4:
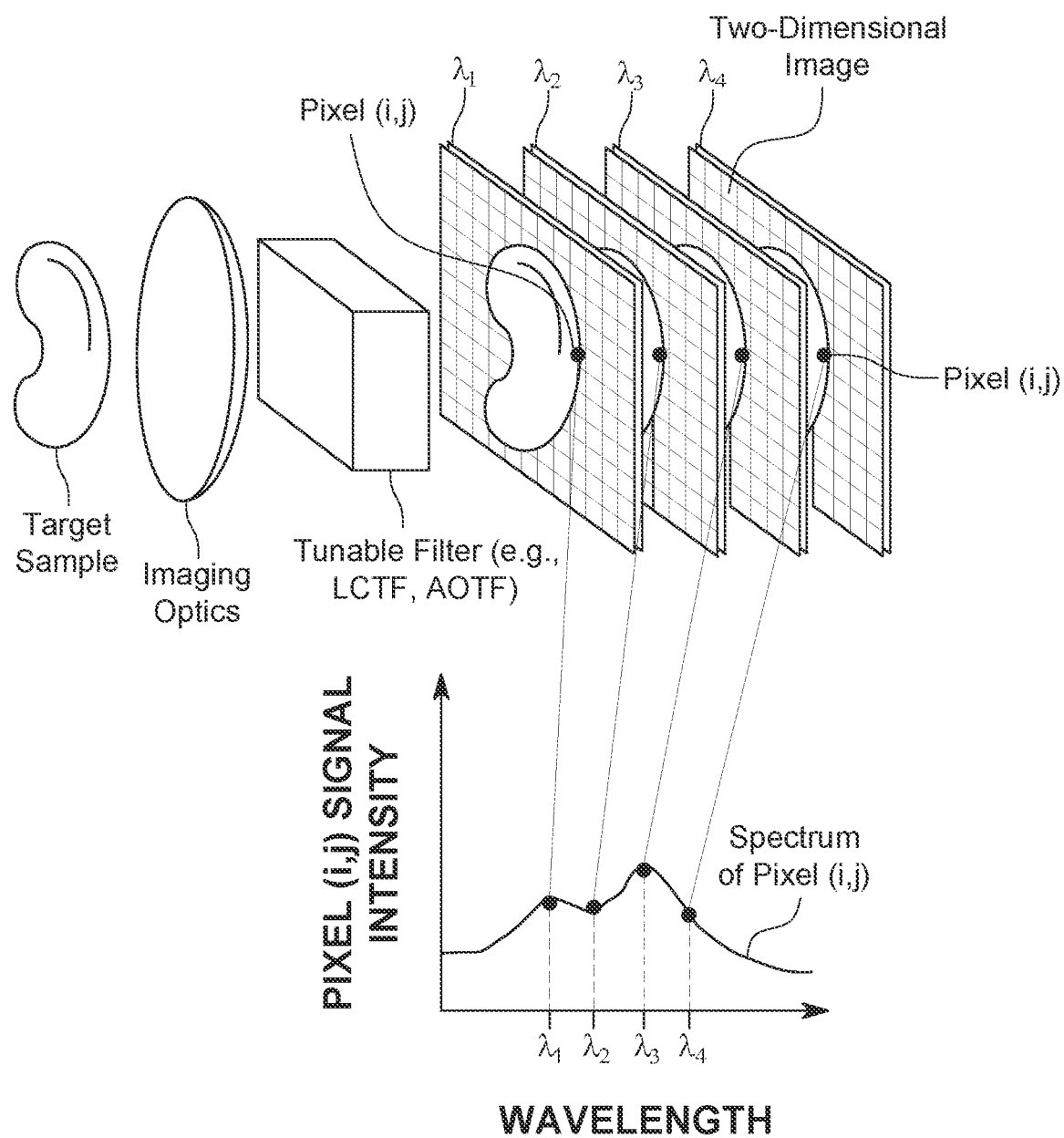
FIG. 4 is a schematic illustration of a 3D Spectral Data Hypercube produced by a Raman Hyperspectral Imaging System (HIS).
Figure 5:
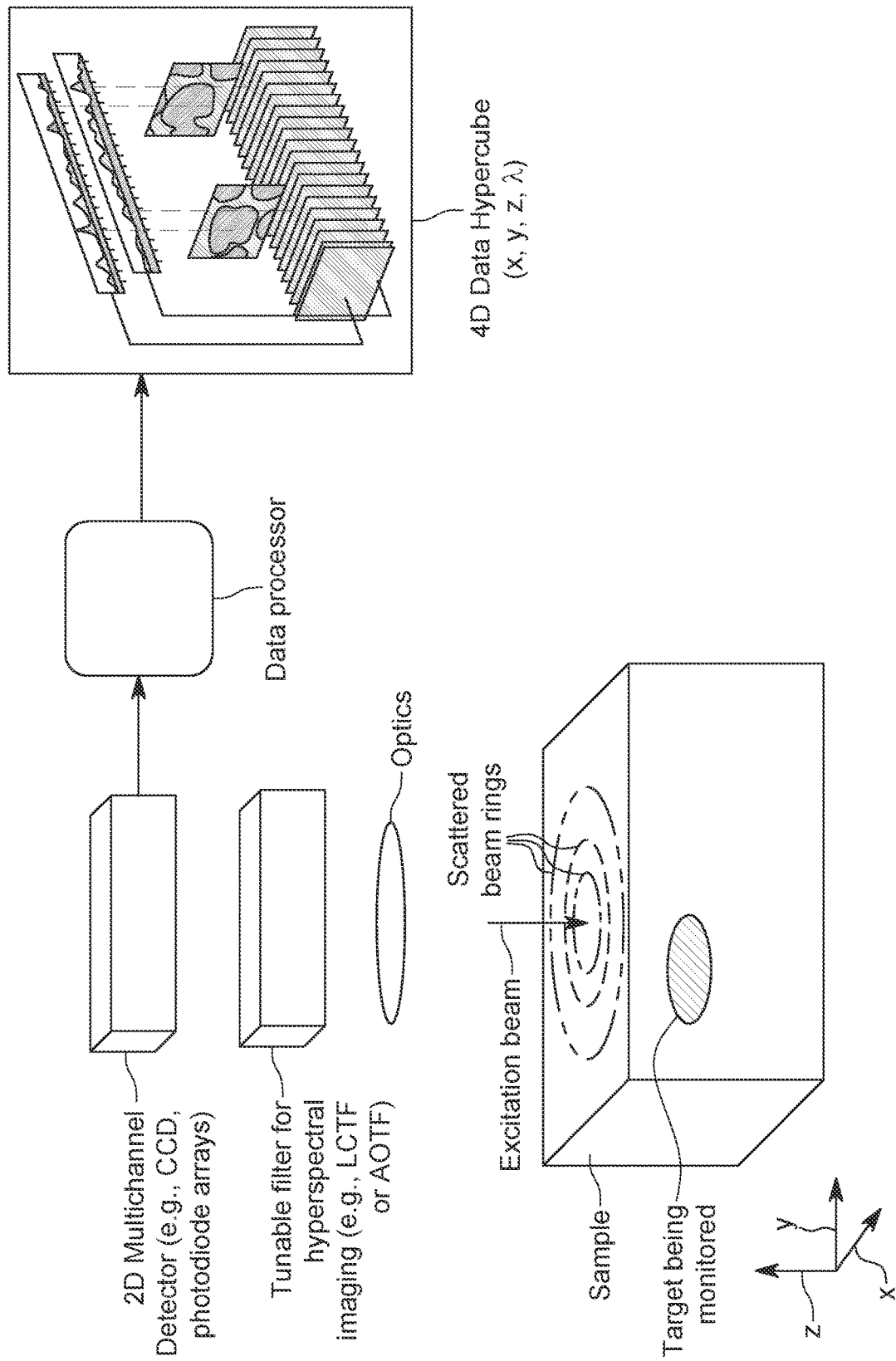
FIG. 5 is a schematic diagram of ORCHID with Hyperspectral Imaging Yielding 4D Data Hypercube (x, y, z, k).

With conventional spectroscopy, the SERS signal at every wavelength within a spectral range is recorded, but for only a single analyte spot. In contrast, Hyperspectral Surface-Enhanced Raman Imaging (HSERI) combines two recording modalities and permits recording of the entire emission for every pixel on the entire image in the field of view using a rapid wavelength-tuning solid-state device such as an acousto-optic tunable filter (AOTF) or a liquid crystal filter (LCTF). Hyperspectral imaging provides a "3D data hypercube" of spectral information from the entire image at a series of wavelengths of interest. FIG. 4 is a schematic illustration of a 3D Spectral Data Hypercube produced by a Raman Hyperspectral Imaging System (HIS). Using tunable solid-state filters, the hyperspectral imaging system collects an entire SERS spectrum for each point of an image, producing a 3D data hypercube (x, y, Raman frequency) of information. Hyperspectral imaging is faster than traditional Raman mapping, which consists of detecting Raman scattering from a single spot and moving the sample to obtain spatial information. By applying hyperspectral imaging, SERS maps of nucleic acid biotargets can be rapidly recorded to monitor metabolic pathways in whole sample systems. FIG. 5 is a schematic diagram of ORCHID with Hyperspectral Imaging Yielding 4D Data Hypercube (x, y, z, k). The system includes a 2D multichannel detector (e.g., CCD), a tunable filter for hyperspectral imaging, and a data processor.

Spatially Offset Raman Spectroscopy (SORS) can be used to probe the molecular composition of a sample that is especially thick and turbid. The concept of source and detector separation has been implemented in a variety of ways, most commonly with a physical separation between the excitation and collection points to provide depth-related spectral information for one dimension (Z). The ORCHID system uses the multichannel imaging capability of a CCD where spatial offsets are directly mapped and digitally binned in selected regions on the 2D (XY) imaging array detector to produce 3D data (XYZ) with depth information.

Furthermore, the use of liquid crystal tunable filters leverages the hyperspectral imaging approach where each image can be scanned spectrally through multiple wavelengths, thus producing a four-dimensional (4D) data hypercube (XYZ, wavelength). The ORCHID system and method has a simple configuration and makes use of the unique advantages of a Liquid Crystal Tunable Filter (LCTF). The tunable filter device can be used to scan across a sample to obtain a hyperspectral hypercube map containing data in 3 axial directions and 1 frequency direction. Using ORCHID, spatially offset Raman spectroscopy at single points and at points within up to a 100 $mm^2$ area are possible. These capabilities can allow larger sample imaging and provide molecular information in different dimensions. In embodiments, the ORCHID system can obtain signal up to half a centimeter. The Z resolution is dependent on the type of sample, level of scattering, and quality of the detector. Spatially offset Raman spectroscopy has a theoretical resolution in the order of centimeters and can feasibly be achieved with the ORCHID system.

A person having ordinary skill in the art will understand that signal shape and intensity are highly variable. Moreover, attempts at calibration based on a simple gel phantom have resulted in models that are not transferrable to more complex samples containing non-Raman signal and background noise or those that have an irregular shape with different boundaries between layers. Furthermore, intrinsic fluorescence background has been a technical hurdle in applications of SORS in-vivo and has limited its usefulness to samples that already have a strong intrinsic Raman scattering property such as bone.

The ORCHID system offers a way to overcome some of the issues encountered by conventional technology by taking advantage of emission signals of particles that exhibit sharp and identifiable spectral peaks, such as SERS gold nanostars and quantum dots. Additionally, the scanning and binning imaging process used in the ORCHID method can be used to localize signals to specific areas. In embodiments, in cancer and other disease diagnostics, this approach can be used for detecting tumors by taking advantage of the well-known enhanced permeability and retention (EPR) effect, which involves the natural propensity of nanoparticles to accumulate in and around cancer cells. To that end, the ORCHID system can be used to create a hyperspectral SERS dataset in multiple spatial dimensions that gives information that can help delineate non-tumor tissue from tumor tissue.

Another application of the ORCHID system is to detect functional probes for in vivo sensing and imaging to allow selective and sensitive monitoring of gene biotargets and molecular processes in whole plant systems. Such an application can be useful for renewable energy research and development. Understanding exactly which genes turn on inside a plant is critical to fine-tuning plant growth for biofuel production.

Small RNAs called microRNAs, regulate gene expression in plants. Usually, biologists must take a sample of the plant, extract the RNA from the sample and use laboratory-based assays such as PCR to determine microRNAs the plant is producing to monitor which genes are active. Advantageously, ORCHID can be used for in vivo intracellular detection of gene expression biomarkers by utilizing sensors for sensitive and selective detection of microRNA biotargets in intact living plants. Exemplary sensors include plasmonics-active inverse molecular sentinel (iMS) nanoprobes based on SERS. The ORCHID technology can establish a basis for functional in vivo imaging of nucleic acid biotargets inside living plants, a tool to potentially revolutionize bioengineering research by allowing the study of such biotargets with previously unmet spatial and temporal resolution.

Acquiring multiple dimensions of data can be tedious. Thus, the ORCHID system uses optimization in the scanning methodology. Creating a high-resolution multidimensional hypercube of the entire sample at high-speed can present challenges. Tradeoffs between data collection time and data volume are made based on the needs of the application. The ORCHID system has a theoretical resolution set at the optical resolution limit dictated by the objective lens and the laser wavelength used. At near-IR wavelengths, the theoretical resolution can be around 0.7 to 1 µm range for the typical epi-illumination microscope in the XY plane. However, mechanical limitations to the physical scanning of the stage itself can slow collection time. For the configuration used for the Examples, a standard microscope stage that had a typical movement speed of around 200 mm/s was used. Faster scanning can be achieved by using high speed stages or alternatively galvanic mirrors, both of which can decrease the data collection time by orders of magnitude.

When using the ORCHID system, signal quantification can be tuned. The different spatial offsets have different signal-to-noise ratios (SNRs) since larger spatial offsets contain more pixels in a larger circle to receive the outgoing Raman/luminescence photons. Testing showed that there is an optimized radial offset distance that maximizes the signal corresponding to the depth of a target. Thus, the depth of the sample can be correlated to the ORCHID signal collected. An important factor to consider, however, is that the SNR gradually decreases as well in the larger radial binning due to the signal becoming more spread out along the binned pixels. One way to increase SNR is to increase the binning thickness, but this comes at the cost of depth resolution due to mixing of signals along the layers as more of the axial positions are sampled.

The ORCHID system can be effectively used to probe deeply embedded targets in highly scattering tissue. Thus, in embodiments, the ORCHID system can be used as a cancer detection mechanism for in vivo tissue sensing. Use in this way can be advantageous because current modalities (e.g., PET, MRI, CT) are prohibitively expensive or come with trade-offs, such as the lack of molecular information. The ORCHID system and method is suitable for use with optical techniques exhibiting narrow-band structures, such as Raman scattering, luminescence from quantum dots, rare earth species, and upconverting nanomaterials. ORCHID combines the strengths of the digital spatial offset concept, hyperspectral imaging, and digital image binding and collation to create a dataset containing information ranging from spatial distribution to molecular makeup. For example, the ORCHID system can provide a real-time monitoring and detection system for cancer margin detection when used to detect gold nanostars that accumulate preferentially in tumors due to the EPR effect. Applying the ORCHID system with SERS gene nanoprobes would provide a potential future in which gene expression can be monitored in-vivo in tissue or plant systems.

In embodiments, the ORCHID system combines the configuration of an epi-illumination microscopy setup coupled with distinct data processing that digitally obtains depth information. FIG. 3C, introduced above, is a schematic diagram of the ORCHID instrumental system. The combination of microscopy scanning and digital Spatially Offset Raman Spectroscopy can be used to resolve the 3D map of gene expression. In embodiments, the ORCHID method includes data processing of a multidimensional hyperspectral data hypercube: two spatial dimensions, x and y, provided by stage scanning, z dimension provided by SORS, spectral dimension (Raman frequency) provided by scanning the liquid crystal tunable filter (LCTF), and Raman signal intensity collected by each pixel of the CCD.

As shown in the schematic of FIG. 3C the ORCHID system includes a typical epi-illumination setup in which a 785-nm continuous wave (CW) laser light source is collimated using a collimating lens and cleaned up with a laser line filter before being routed through a dichroic filter toward the objective where the light is focused into the sample from below. The Raman signal from the sample travels the path back to a dichroic mirror that reflects the signal across a liquid crystal tunable filter (LCTF) (Perkin Elmer used in Examples) for wavelength selection and finally into a charge-coupled device (CCD) array (Princeton Instruments used in Examples).

For the ORCHID system, the spatial offset for Z depth resolution is achieved by the process of binning pixels at specific radial distances away from the center of the CCD array (i.e., where the laser excitation point is located). A pixel size can be changed by combining pixels into larger superpixels. The combining of pixels is known as binning. When binning, squares of pixels are 'binned' into larger pixels. For example, for a 2×2 bin, a square of 2×2 (4) pixels are read out as if they were a single pixel. Benefits of binning can include improved signal-to-noise ratio (SNR) and increased frame rate (acquisition speed). The SNR is improved as the read noise is only added to each superpixel. For example, in a 2×2 bin, the signal is improved by four times (as each superpixel is four pixels), meaning the SNR is boosted by a factor of 4:1 (signal:noise). Increased SNR improves the ability to image weak signals because the device is far more sensitive.

FIG. 3B is an illustration showing a CCD array configuration consisting of a 512 by 512-pixel array with each pixel element having a 10-µm width. As shown in FIG. 3B, pixels can be binned in circular rings around the center point of excitation. Digital Spatial Offset is a concept where photon signals of collection "radii" can be selected digitally by binning appropriate pixels of the two-dimensional CCD to represent different source-detector separations. A sequence of images at multiple wavelengths is obtained by scanning the LCTF at 200 or more wavelengths at nm resolution. The resulting data are a hyperspectral data hypercube containing both high resolution spatial (x,y) and spectral information (Raman v).

The ORCHID system used in the Examples was programmed using the Python programming language (Version 3.7.5) with direct device interfacing for the camera, stage, and filters. Data treatment and analysis for forming the images and spectra were done with Python using the Numpy and Matplotlib libraries. Finalized graphs were created using GraphPad Prism. The spatial offset data were created by multiplying the collected image sensor data with a simple binary mask of different radial thicknesses. A spectrum was then constructed by summing the binned images across each wavelength to which the corresponding filter was set. Further processing of the spectra used an iterative polynomial algorithm to remove the broad fluorescent background.

EXAMPLES

Example 1

Figure 6:
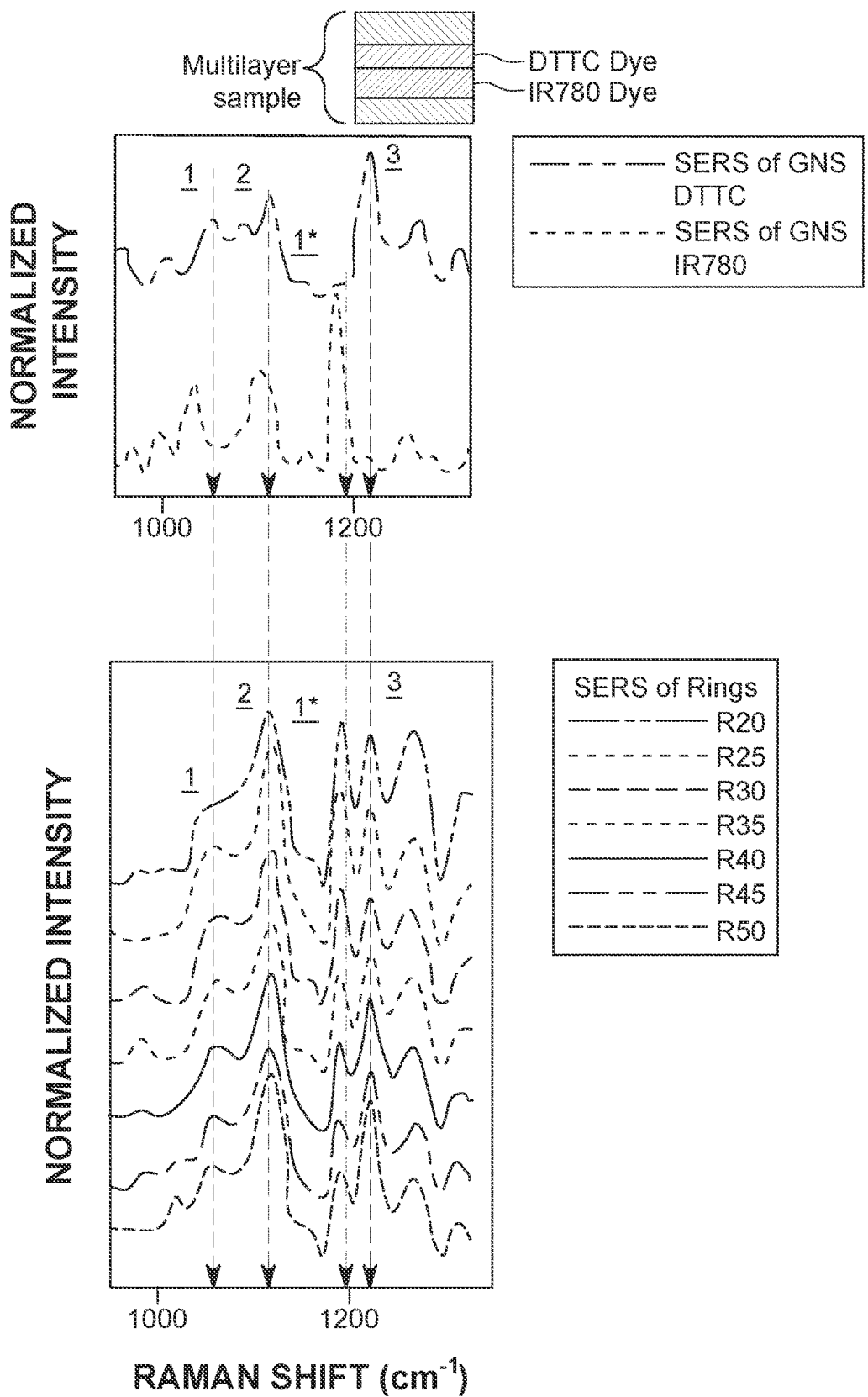
FIG. 6 includes a schematic illustration of the layering of a multi-layer sample, a top spectra showing the specific SERS spectra of IR780 and DTTC, and a lower spectral plot showing a series of Raman spectra with increasing spatial offsets.

Testing was performed to evaluate using the ORCHID system to perform depth dependent multiplex monitoring of signals. An agarose gel multi-layer sample with 3 mm thick layers was used. FIG. 6 shows a schematic representation of the layering of the multi-layer sample. To prepare the gel multilayer sample, first a 3% w/v agarose gel containing a concentration of 0.1 nM particle-dye was embedded on a small 5 cm diameter petri dish. Then, multilayered samples were fabricated by stacking the particle-dye embedded gels onto each other with a very thin layer of agarose gel solution to solidify the layers together.

Two of the layers had silica-coated gold nanostars (GNS) embedded therein. The GNS in one layer were linked to IR780 Raman dye, and the GNS in the other layer were linked to DTTC Raman dye.

All chemicals were purchased from Sigma Aldrich (St. Louis, US). A surfactant free and seed-mediated growth method was utilized to create stable GNS particles. A 12-nm seed solution was first prepared by adding 15 mL of 1% trisodium citrate to 100 mL of 1 mM $HAuCl_4$ solution under vigorous stirring and boiling conditions. Upon the solution's color change from black to red, the mixture was cooled and filtered through a 0.22-µm nitrocellulose membrane. A new solution of 10 mL of deionized water, 10 µL 1 N HCl, and 493 µL $HAuCl_4$ was then prepared and placed under moderate stirring. Addition of 100 µL of 12 nm seed particles, 50 µL of 2 mM $AgNO_3$, and 50 µL of 0.1 M ascorbic acid produced 0.1 nM gold nanostars that were roughly 50 nm in size from tip to tip. More $AgNO_3$ at increased pH levels were added afterwards to create silver coated gold nanostars, which further enhanced the SERS enhancement. The coated particles were produced by adding 10 µL of 29% $NH_4OH$ and 50 µL of 0.1 M $AgNO_3$. The solution color changed from blue to brownish red. The particles were subsequently mixed with 10 µL of 1 mM of a SERS dye, either DTTC or IR 780. The particles and dye were then enclosed together with the addition of tetraethyl orthosilicate (TEOS). After a brief wash and resuspension in 1 mL deionized water, the silica coated particle dye combination was capped off with the addition of 100 µL of 1 mM 1 k polyethylene glycol (PEG) solution.

In the gel multilayer, the IR780 Raman dye was in the layer closer to the excitation spot. The DTTC Raman dye was in the layer farther away from the excitation spot. The different Raman dyes exhibited specific and different SERS spectra. The top spectra in FIG. 6 shows the specific SERS spectra of IR780 and DTTC.

The ORCHID system collected a single hyperspectral data hypercube in 3 seconds each for each Raman frequency under 785-nm laser excitation at 100 mW power. Each spectral image for a specific Raman frequency (defined by the LCTF) was then passed through a radial binning mask corresponding to a specific spatial offset ring and summed to a single value. These values at multiple Raman frequencies were then collected to provide a series of Raman spectra (each spectrum being associated with a specific spatial offset "ring" labeled "Rn"). FIG. 6 lower spectral plot provides a series of Raman spectra with increasing spatial offsets. The plot in FIG. 6 lower shows that with increasing spatial offsets ("R" with increasing numbers), different contributions of the two Raman spectral signatures of IR780 and DTTC appear. As can be seen in FIG. 6, for the smaller offsets, the spectrum was mainly dominated by peaks from the lower layer closer to the excitation spot (GNS-IR780 layer). With increasing offsets, more SERS signal contribution of the upper layer (GNS-DTTC layer) began to appear more prominently as the greater offsets increased the collection bias towards photons that had travelled further, thus demonstrating the concept of depth-dependent multiplex monitoring.

Example 2

Figure 7A:
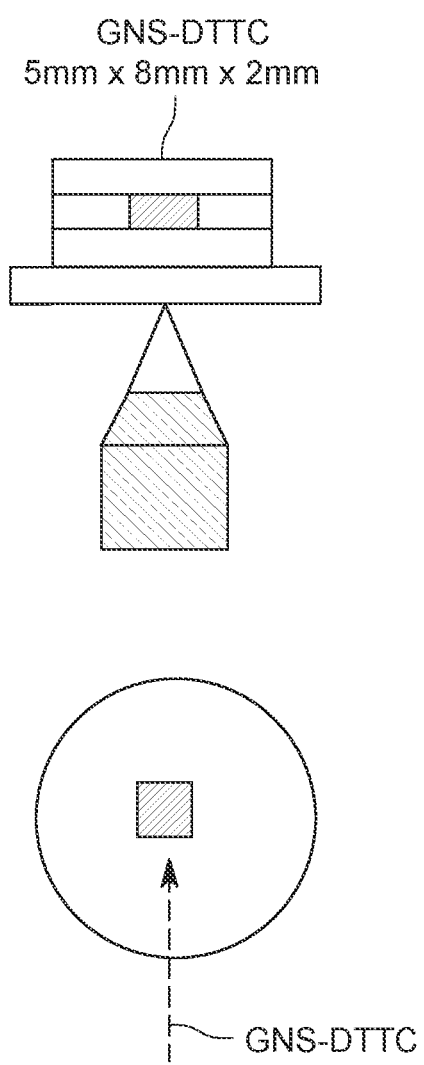
FIG. 7A is a schematic diagram of GNS-DTTC embedded in an agarose gel sample.

In this example, the ORCHID system was used to produce a hyperspectral spatial map of a sample system, which included an agarose gel sample with an embedded layer containing gold nanostars linked with a DTTC Raman Dye (GNS-DTTC) in the middle. FIG. 7A is a schematic diagram of GNS-DTTC embedded in an agarose gel sample. The GNS-DTTC was a small 5 mm×5 mm hypercube sandwiched between 2 mm thick gel layers.

As discussed above, SERS-labeled GNS injected into a mouse model preferentially absorb into tumors due to the enhanced permeability and retention (EPR) effect of tumor vasculature. In this study, the agarose gel simulated a tissue sample and the GNS-DTTC hypercube represented a tumor that had absorbed GNS nanoprobes.

Figure 7B:
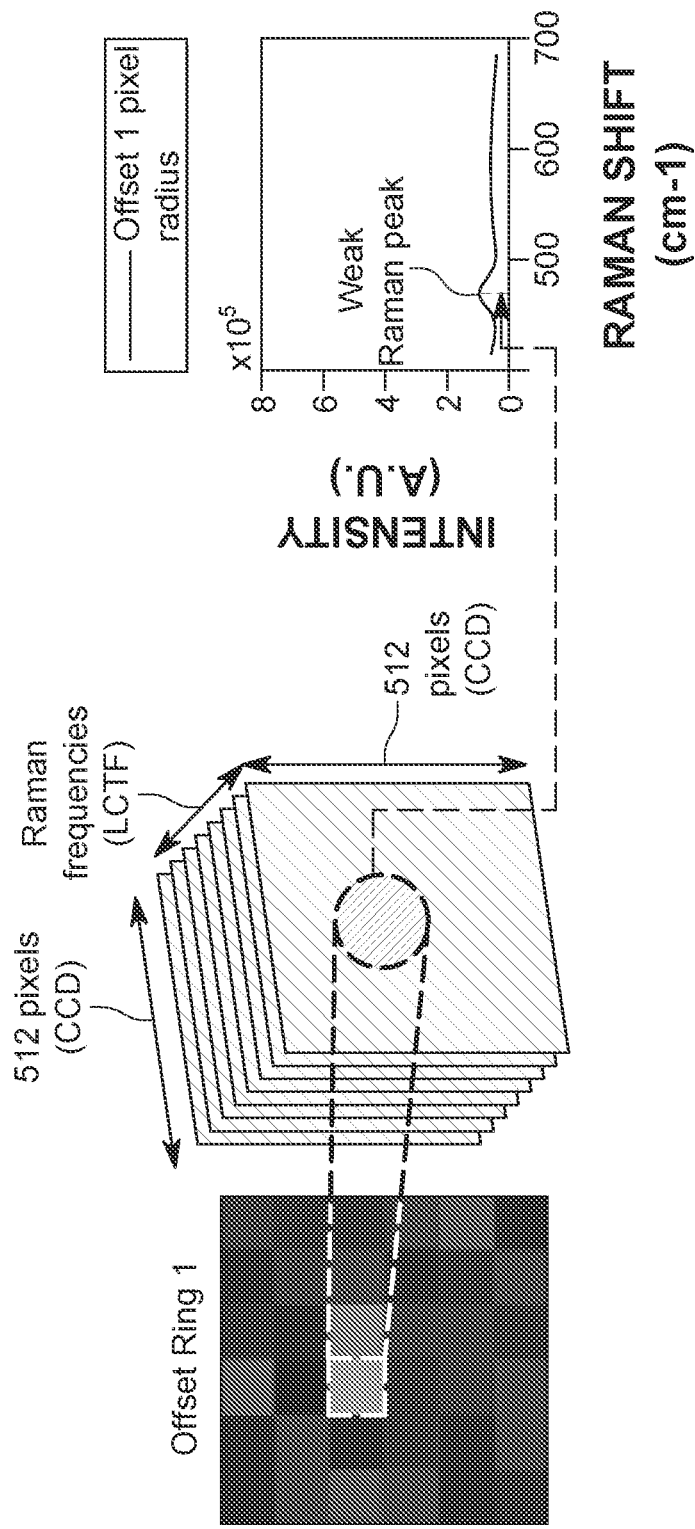
FIG. 7B is a hyperspectral imaging map of a sample showing high Raman signal collection with a spatial offset at offset ring 1.
Figure 7C:
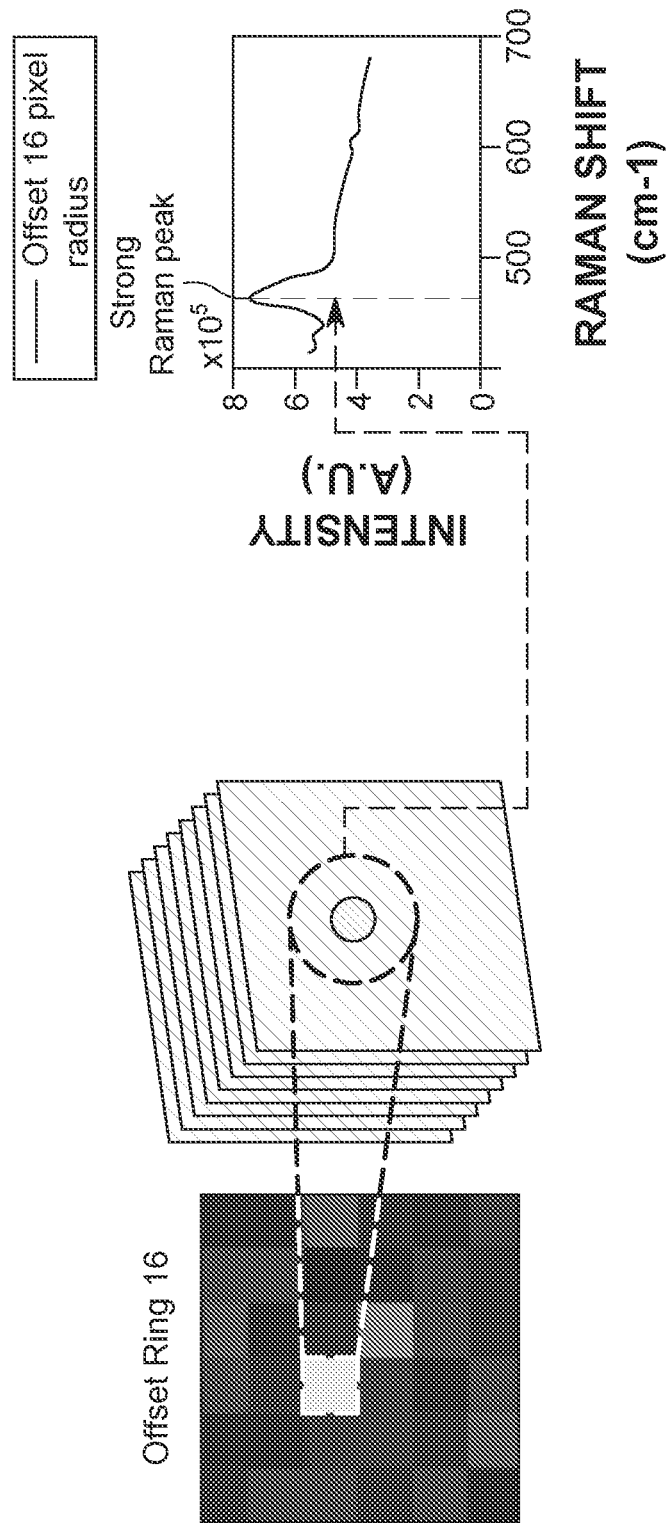
FIG. 7C is a hyperspectral imaging map of a sample showing high Raman signal collection with a spatial offset at offset ring 16.
Figure 7D:
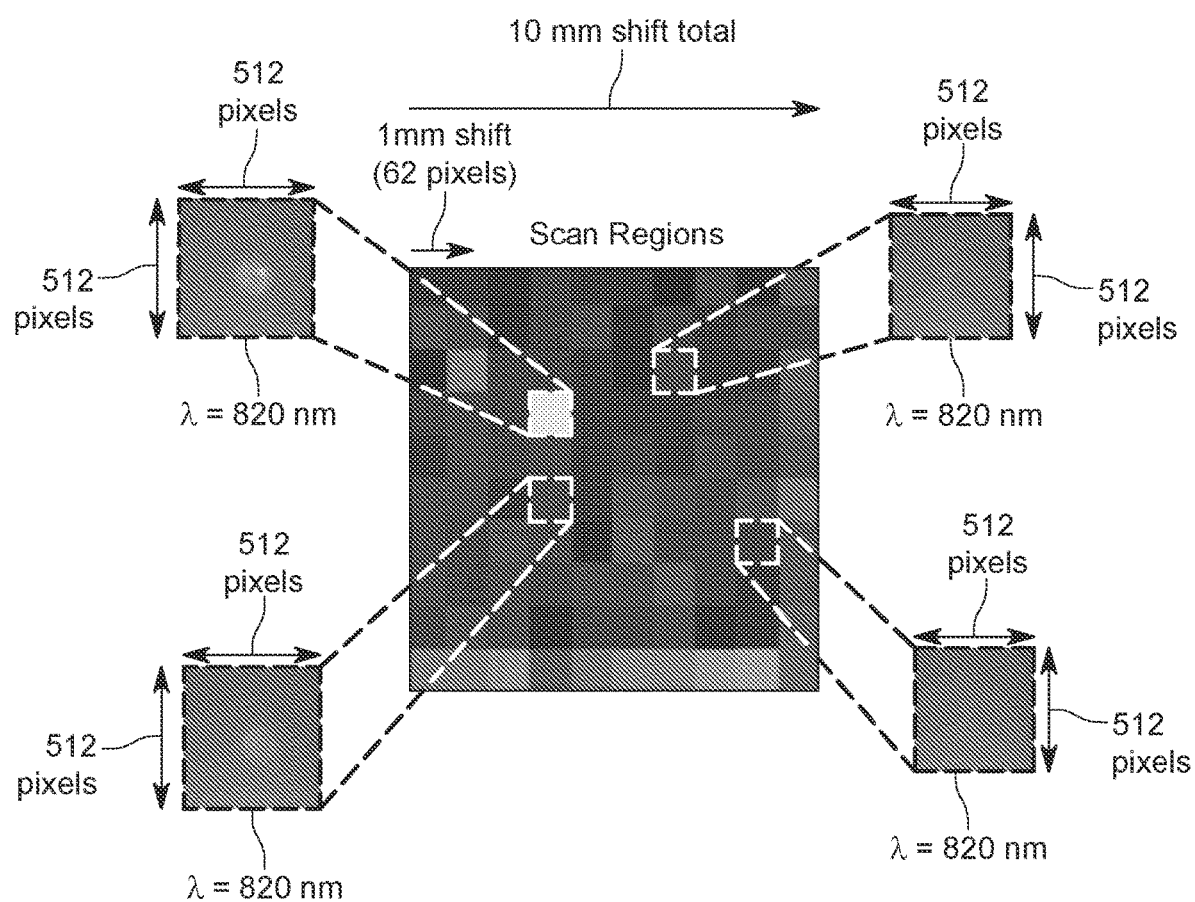
FIG. 7D is a spatial map showing individual collected images at the Raman peak frequency (497 cm$^{-1}$).

The ORCHID system was scanned across the sample spatially and spectrally as a means of spatially localizing the XY position of the GNS-DTTC hypercube. During scanning, the stage was moved at increments of 1 mm and the LCTF wavelength was scanned at increments of 1 nm from 800 nm to 830 nm. The exposure was set to 1 second and selected to capture the data at each combination of spatial and spectral position. A slice at 820 nm of the stitched hyperspectral data hypercube is shown in FIG. 7C. The area on the map enclosed by a square shows the position of the GNS-DTTC volume whose SERS spectra has a local peak at 820 nm. FIGS. 7B and 7C are hyperspectral imaging maps of the sample showing high Raman signal collection with greater spatial offset. FIG. 7B is an imaging map at offset ring 1, and FIG. 7C is an imaging map at offset ring 16. The hyperspectral hypercube data was processed across different frequencies and subsequently binned and summed to produce the Raman spectra. The radially binned pixels were summed as a total intensity corresponding to a scanned location. FIG. 7D is a larger spatial map showing the individual collected images at the corresponding Raman peak frequency (497 $cm^{-1}$). The central image represents the total scanned images collected where each data point on the image represents the sum of the spatially offset CCD image pixels corresponding to a selected binning radius. The brighter data points in the 2D image correspond to higher intensity values of GNS-DTTC gel.

Example 3

Figure 8:
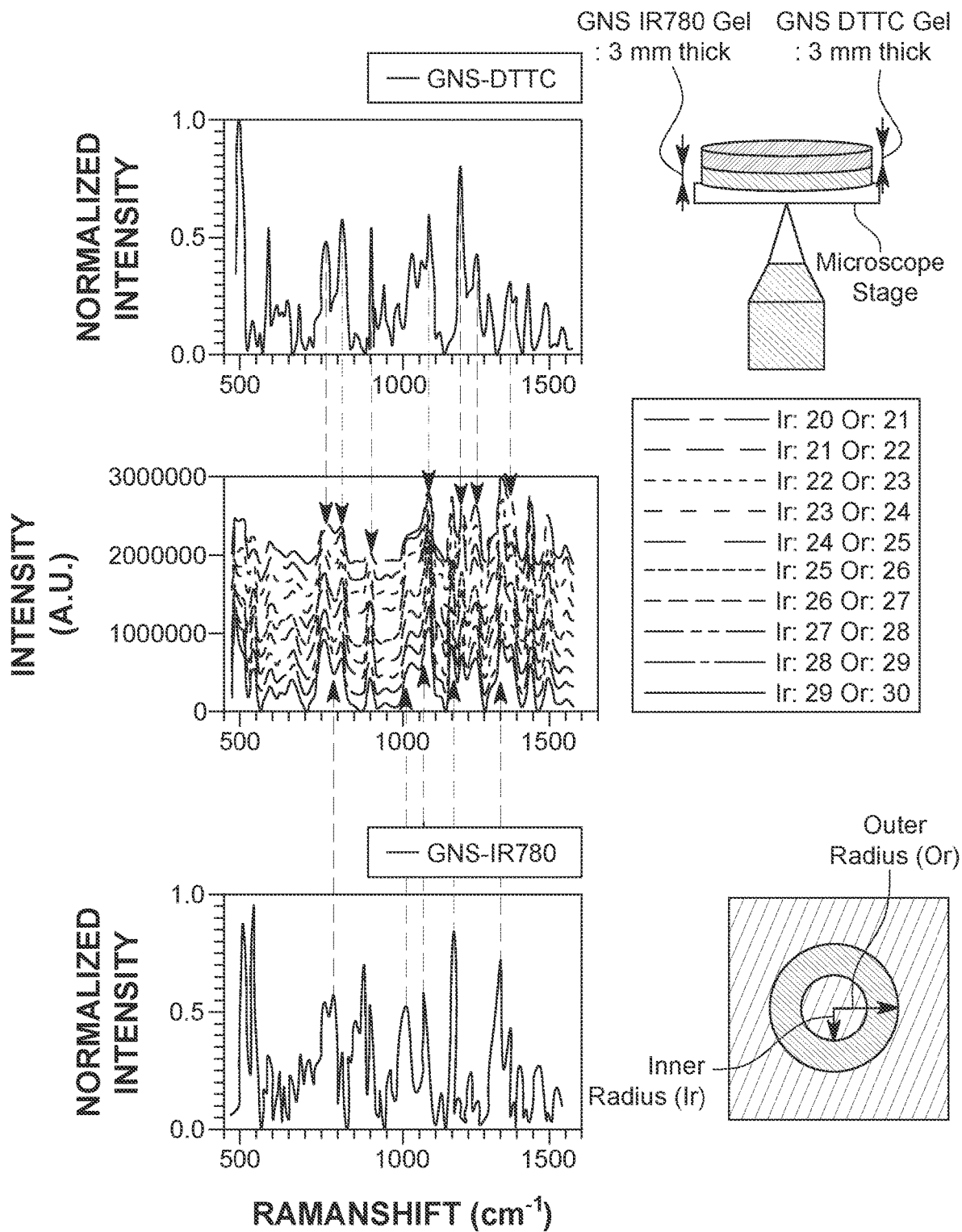
FIG. 8 shows a "waterfall" collection of different spatial offset spectra illustrating the change in spectral shape across increasing spatial offsets.

A simplified dual-layer gel sample of GNS-DTTC and GNS-IR780 that was stacked was used to illustrate the digital radial binning concept for in depth sensing. Each layer was 3-mm thick. The GNS-IR780 layer was the bottom layer, and the GNS-DTTC layer was the top layer (FIG. 8). The layers were stacked and probed with the ORCHID system at different spectral frequencies. Hyperspectral data were collected at a single spot, where the LCTF was scanned from 800 nm to 880 nm. The resulting image arrays were computationally masked at different radial distances, representing spatial offsets by the distance of multiple 12 μm pixels in a similar way to the digital spatial offsets shown in FIG. 3B.

In FIG. 8, a "waterfall" collection of different spatial offset spectra shows the change in spectral shape across increasing spatial offsets. In FIG. 8, the plot labels Ir (Inner radius) and Or (Outer radius) are the spatial offset binning. Above and below the waterfall plot are the reference GNS-dye spectra with arrows pointing to the unique peaks in each dye. In particular, the prominence of SERS peak belonging to one or the other GNS-dye changes indicating the ability of the system to discern between layers of the SERS targets of at least 3 mm. With greater spatial offset radial binning distances, the Raman peaks of the farther layer become more apparent, demonstrating that recovery of the Raman spectra from the deeply embedded layer is possible.

Example 4

Figure 9:
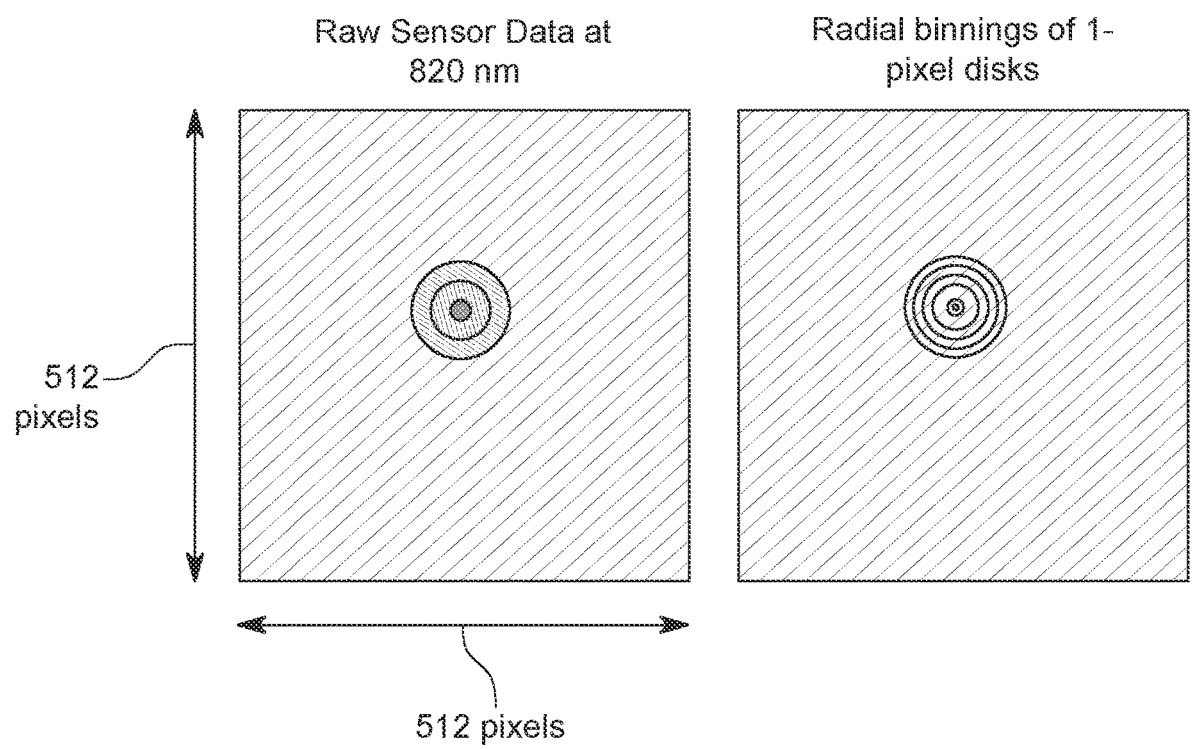
FIG. 9 illustrates the image array and binary mask used to spatially bin the image data.
Figure 11A:
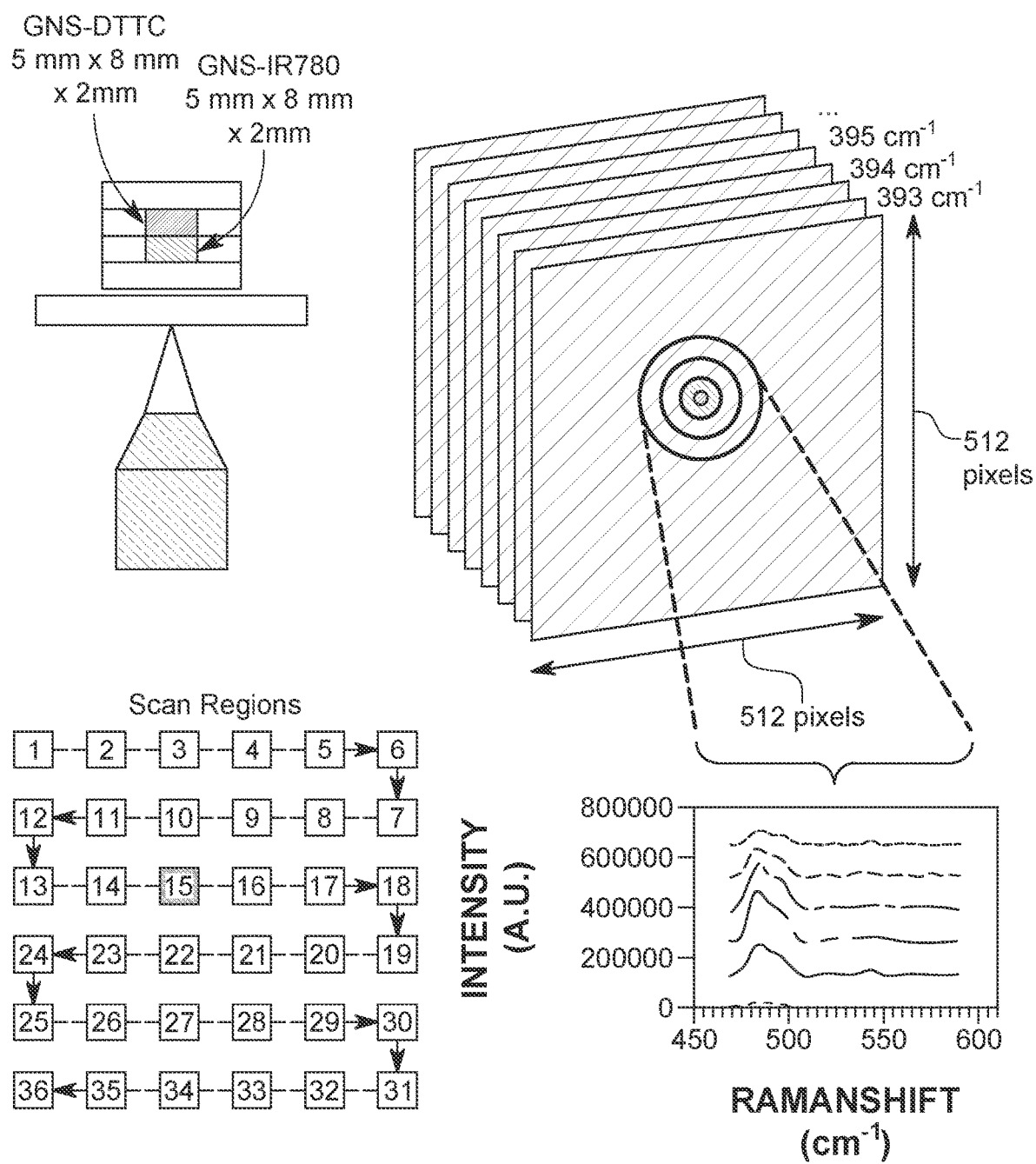
FIG. 11A is a schematic representation of a sample used for testing.

An embedded dual layer sample sandwiched between 5 mm thick gel layers was used to demonstrate the mapping capabilities of ORCHID. FIG. 11A is a schematic representation of the sample used for this testing. The XY plane mapping was combined with the binned radial spatial offsets. FIG. 9 illustrates the image array and binary mask used to spatially bin the image data. For FIG. 9, the raw sensor output was captured at 820 nm and the binary radial mask was used to selectively choose spatially offset pixels.

Figure 11B:
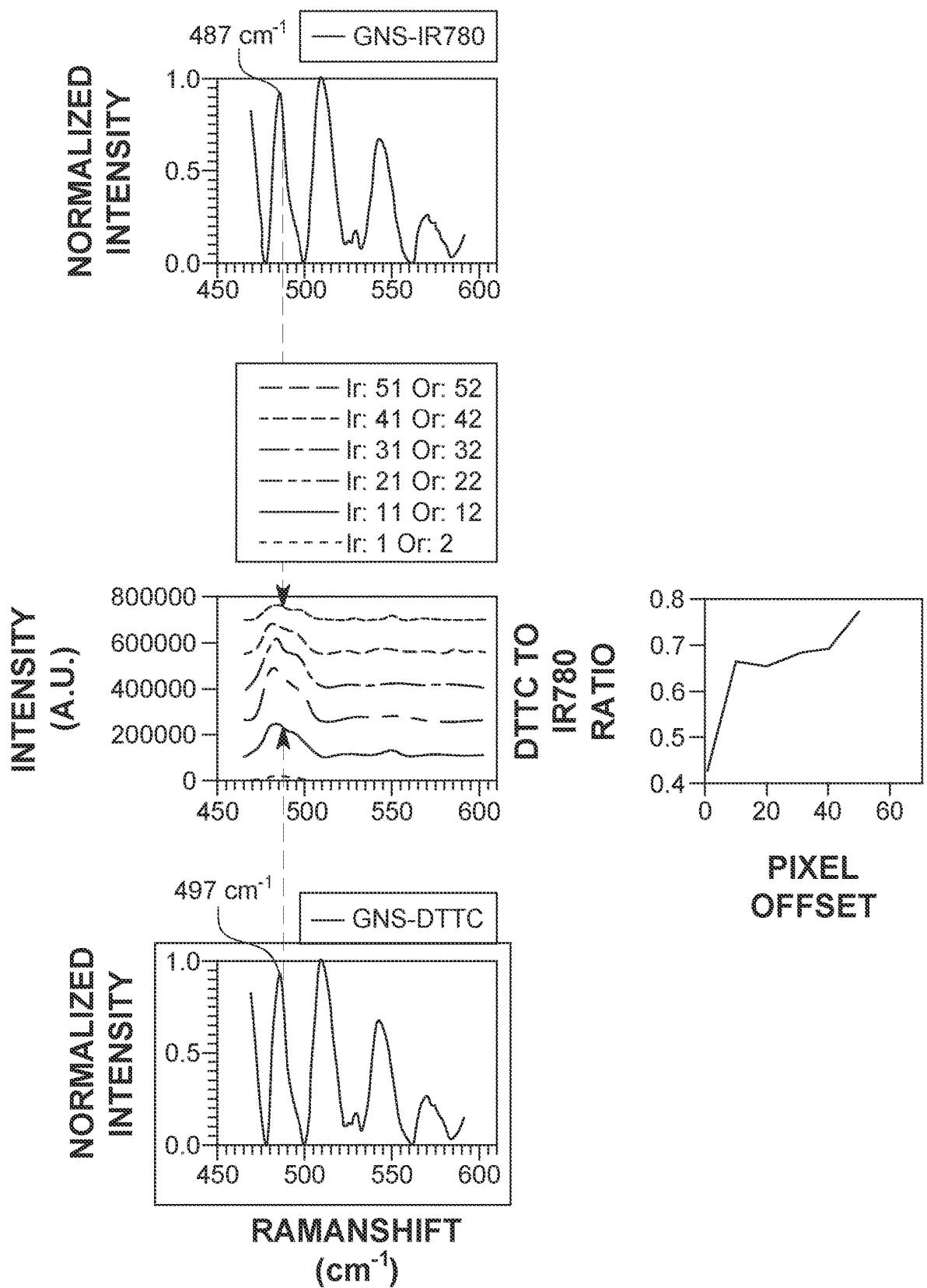
FIG. 11B is a hyperspectral data map.

Two 5 mm thick gels containing GNS-DTTC and GNS-IR780 were stacked and embedded between 5 mm thick gel layers and subsequently probed with the ORCHID system at different spectral frequencies. The resulting Raman spectra were obtained in the highlighted region containing the stacked GNS-dye sample. FIG. 11B is a waterfall plot comparing the different inner and outer radial offsets with the respective reference spectra of each dye above and below. Jr and Or stands for inner radius and outer radius respectively and represent the spatial offset disks. As in previous examples, increasing spatial offsets resulted in the farther away GNS-DTTC signal becoming more prominent.

Figure 10A:
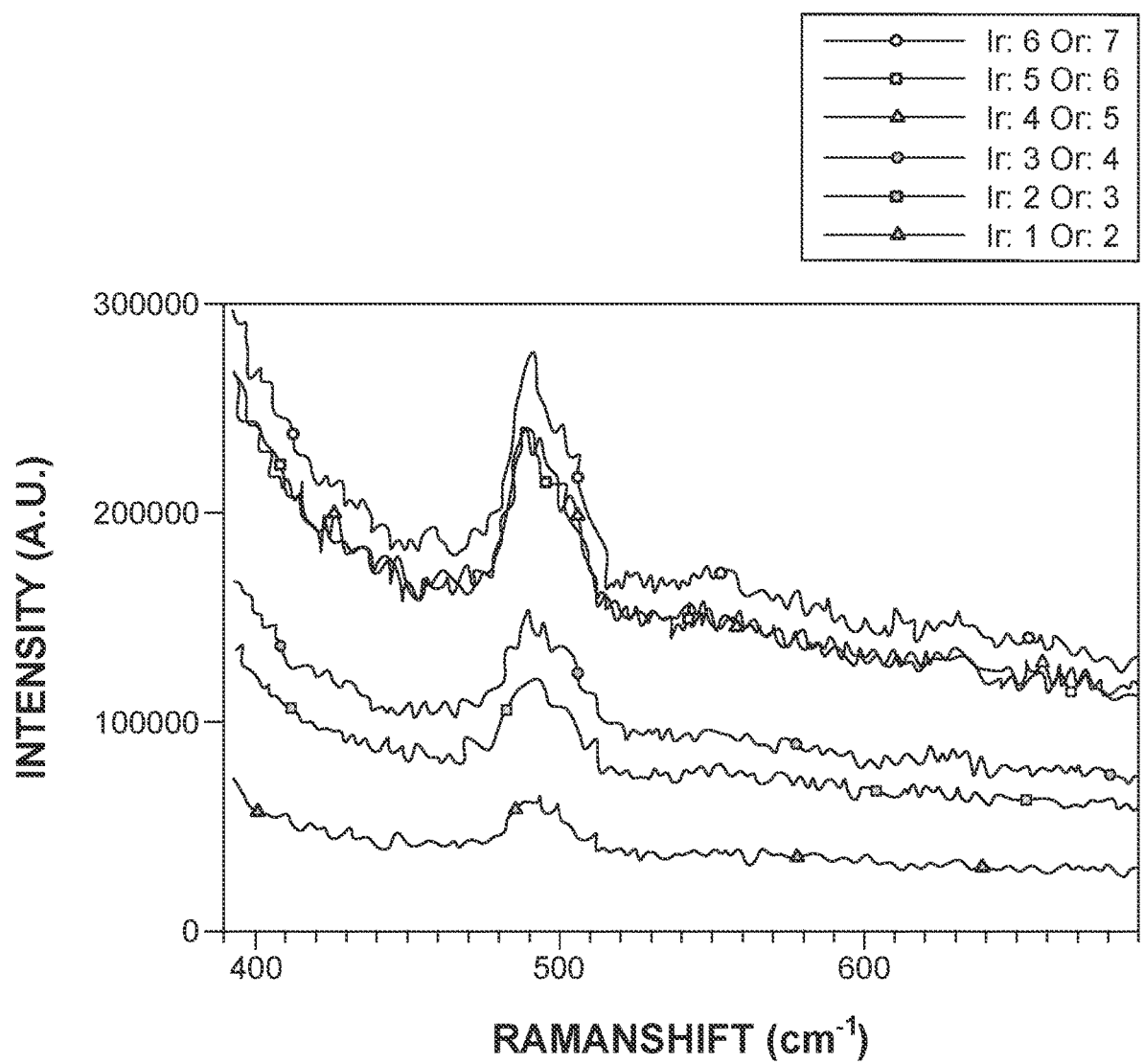
FIG. 10A and FIG. 10B are spectral plots of alternative spatial offset configurations with radial binning configurations for the embedded two-layer SERS gel phantom used in Example 4.
Figure 10B:
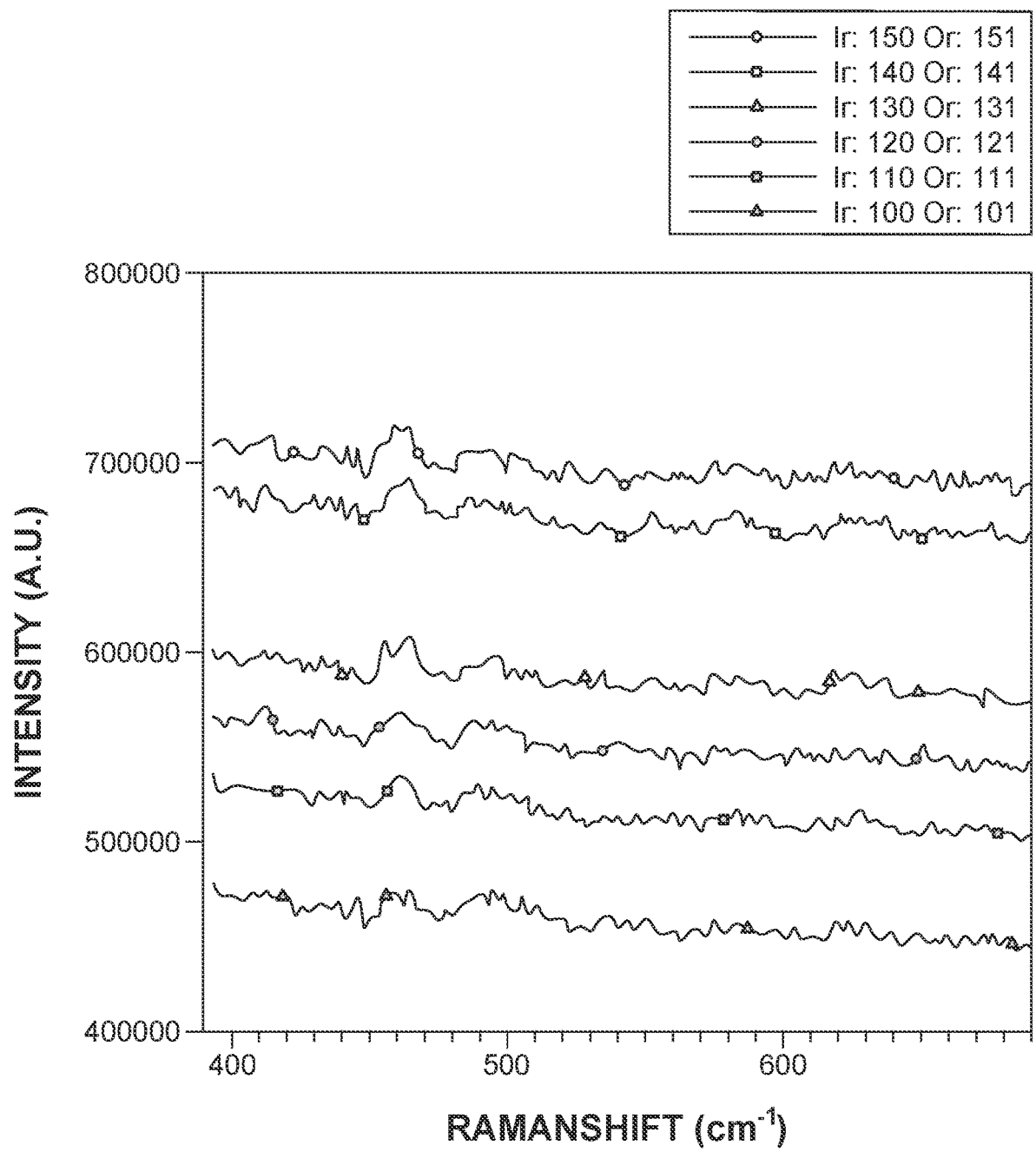

Data were collected in a similar manner as the previous examples but for this example, the data were formed together to make a hyperspectral data map (FIG. 11B). With the spectral peaks of each GNS-dye identified, a ratio-metric graph of between the dye peaks of GNS-DTTC and GNS-IR780 was depicted to show the spectral change as the spatial offsets were increased (FIG. 11B). For this example, additional spatial binning configurations are shown in FIGS. 10A and 10B. FIGS. 10A and 10B are spectral plots of alternative spatial offset configurations with radial binning configurations for the embedded two-layer SERS gel phantom used in Example 4. Ir and Or stand for inner and outer radius of the binning disk used on the raw captured image. The smaller configurations have a much lower signal to noise ratio because there are less pixels to collect light, which can lead to irregular spectral shapes. The data ultimately showed the prevalence of the farther layer GNS-dye with greater offset in agreement with the ORCHID concept.

Example 5

Figure 12:
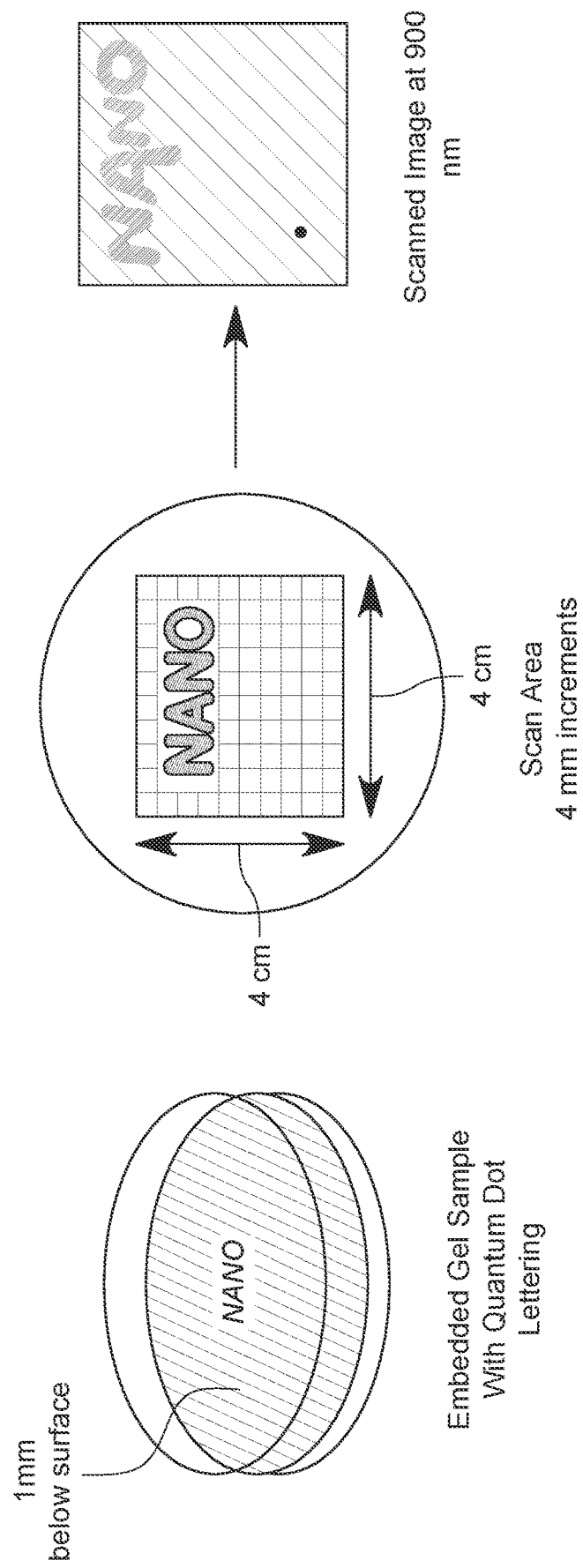
FIG. 12 is a schematic representation of a sample.

The ORCHID system can be used to resolve objects in the XY plane. In this example, a gel sample was infused with quantum dots in the form of the word "NANO" about 1 mm below the surface of the gel. Quantum dots with a PbS core and emission peak wavelength at 900 nm were used in the gel lettering. FIG. 12 is a schematic representation of the sample, which was contained in a petri dish and raster scanned across a 4 cm×4 cm area at 4-mm stage movement increments. Data were collected at 100-ms exposure times. In this example, the resulting image shows that the ORCHID system can resolve millimeter scale features such as the letters.

Figure 13:
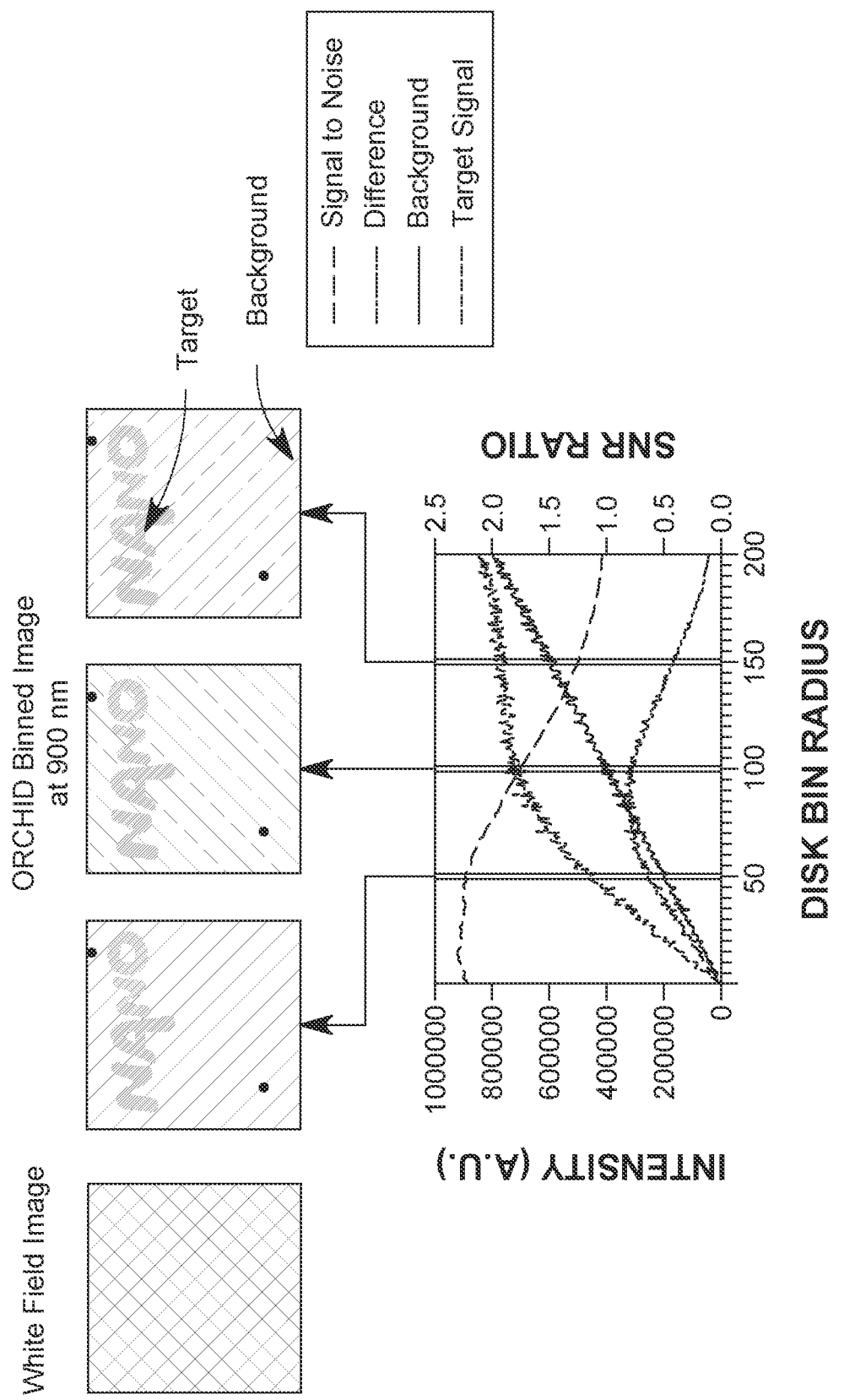
FIG. 13 shows plotted comparisons of target signal pixel regions (inside the "NANO") and background pixel regions as a function of disk binning radius (of 1 pixel width) used to form raw images.

The images obtained with the ORCHID system were binned separately using different varying disk radii, increasing in 1 pixel width increments. FIG. 13 shows plotted comparisons of target signal pixel regions (inside the "NANO") and background pixel regions as a function of disk binning radius (of 1 pixel width) used to form the raw images. A pixel region where the target signal was located (i.e., within the word "NANO") is plotted versus the bin radii to show the effect of the peak radial bin on signal collection parameters: target signal, background signal, difference absolute signal (i.e., background-subtracted target).

The target signal is the photon count collected at the location of quantum dots, for example at the letter "A" as indicated in FIG. 13. The background signal is the photon count collected at an area without quantum dots (i.e., outside the word "NANO"). The background signal, represented in FIG. 13, increased linearly with the bin radius as expected since a larger bin radius corresponds to a larger circle of a binned detection area. On the other hand, the target signal, represented in FIG. 13, initially increased with increasing bin radius, but the rate of increase diminished after the 75-pixel radii leveled off. As a result, the absolute signal (i.e., background subtracted signal), represented in FIG. 13, reached a maximum at around 75-pixel radii. The signal-to-noise (SNR) ratio is also plotted on the right axis. The SNR ratio showed a decrease in signal after 50 pixels of radial binning. The corresponding image at three radial binning configurations are shown above the plot to illustrate the differences in image quality at the respective binning settings, 50 μm, 100 μm, and 150 μm, respectively. FIG. 13 shows that there is a maximum radial offset of around 75 to 80 pixels that maximizes the signal corresponding to the depth of the target (1 mm below the surface). This demonstrates the ability to correlate depth to the ORCHID signal collected. Corresponding images at 50, 100, and 150 binned radial pixels show correlation with the trend of the signal ratio in the plotted graph peaking at around 80 pixels. An important factor to consider however is that the SNR gradually decreases as well in the larger radial binning due to the signal becoming more spread out along the binned pixels.

One skilled in the art will readily appreciate that the present disclosure is well adapted to carry out the objects and obtain the ends and advantages mentioned, as well as those inherent therein. The disclosure described herein as representative of preferred embodiments, is exemplary, and is not intended as a limitation on the scope of the present disclosure. Changes therein and other uses will occur to those skilled in the art which are encompassed within the spirit of the present disclosure as defined by the scope of the claims.

No admission is made that any reference, including any non-patent or patent document cited in this specification, constitutes prior art. It will be understood that, unless otherwise stated, reference to any document herein does not constitute an admission that any of these documents form part of the common general knowledge in the art in the United States or in any other country. Any discussion of the references states what their authors assert, and the applicant reserves the right to challenge the accuracy and pertinence of any of the documents cited herein. All references cited herein are fully incorporated by reference, unless explicitly indicated otherwise. The present disclosure shall control in the event there are any disparities between any definitions and/or description found in the cited references.

The invention claimed is:

1. A method for spatially locating a target inside a sample and providing spectral information for imaging the target, the method comprising:
    illuminating a laser light source onto a sample to produce a backscattered optical signal-resulting from Raman spectroscopy or luminescence from quantum dots, rare earth species, or upconverting nanomaterials;
    spectrally scanning and detecting the backscattered optical signal at selected spectral increments using a tunable filter to provide three-dimensional spectral information (x, y, wavelength) from the sample at a series of wavelengths of interest;
    providing three-dimensional spatial information (x, y, z) from the sample at a series of spatial dimensions of interest by spatially scanning and detecting the backscattered optical signal to provide spatial data in the x and y dimension at selected increments; wherein the x and y dimension spatial data are binned according to digital offsets based on selected radial pixel distances from the laser light source, and wherein spatial offset techniques are used to provide spatial data in the z direction;
    combining the three-dimensional spectral information and the three-dimensional spatial information to produce a four-dimensional (x, y, z, and wavelength) data hypercube thereby enabling spatial location of the target inside the sample;
    providing to a display at least a portion of the four-dimensional (x, y, z, and wavelength) data hypercube as a plurality of hyperspectral imaging maps;
    applying a spatial offset ring to the four-dimensional (x, y, z, and wavelength) data hypercube to produce a summed value for each wavelength of the series of wavelengths of interest; and
    providing to the display the plurality of summed values as a series of Raman spectra.

2. The method of claim 1, wherein the tunable filter comprises a liquid crystal tunable filter.

3. The method of claim 1, wherein the tunable filter comprises an acousto-optic tunable filter.

4. The method of claim 1, wherein the laser light source is remotely illuminating the sample and the detection is performed remotely.

5. The method of claim 1, wherein the backscattered optical signal is enhanced with Surface-Enhanced Raman Spectroscopy (SERS) nanoparticles.

6. The method of claim 5, wherein the SERS nanoparticles comprise gold nanostars.

7. The method of claim 1, wherein the optical signal comprises luminescence from quantum dots.

8. The method of claim 1, wherein the target is a chemical inside a sample container.

9. The method of claim 1, wherein the target is a lesion or tumor inside ex vivo or in vivo tissue of a human or animal.

10. The method of claim 1, wherein the target is a biomarker or a sensor inside a living plant.

11. The method of claim 10, wherein the sensor is a plasmonics-active inverse molecular sentinel nanoprobe based on SERS.

12. The method of claim 1, wherein applying the spatial offset ring comprises applying at least a portion of each hyperspectral imaging map of the plurality of hyperspectral imaging maps to a radial binning mask corresponding to the spatial offset ring.

13. The method of claim 12, wherein radial binning mask provides at least a four times improvement in a signal-to-noise ratio of imaging the target.

14. The method of claim 1, wherein the laser light source comprises a 785 nanometer continuous wave laser light source.

15. The method of claim 1, wherein the laser light source comprises a collimating lens.

16. The method of claim 1, wherein the laser light source comprises a dichroic filter.

17. The method of claim 1, wherein the four-dimensional (x, y, z, and wavelength) data hypercube has a resolution better than one micron in an xy plane.

18. The method of claim 1 further comprising processing the three-dimensional spectral information using an iterative polynomial algorithm for reducing broad fluorescent background.

19. The method of claim 1, wherein the selected spectral increments include at least 200 wavelength increments.

* * * * *